US012758605B2

(12) United States Patent
Zhang et al.

(10) Patent No.: US 12,758,605 B2
(45) Date of Patent: Oct. 13, 2026

(54) DRUG FOR TREATING UROLITHIASIS-RELATED DISEASE, AND PREPARATION METHOD THEREFOR

(71) Applicant: HONG ZHANG, Sanhe City (CN)

(72) Inventors: Hong Zhang, Sanhe City (CN); Kuiwu Wang, Hangzhou (CN); Qian Gui, Beijing (CN)

(73) Assignee: Hong Zhang, Sanhe City (CN)

( * ) Notice: Subject to any disclaimer, the term of this patent is extended or adjusted under 35 U.S.C. 154(b) by 489 days.

(21) Appl. No.: 18/272,457

(22) PCT Filed: Dec. 29, 2021

(86) PCT No.: PCT/CN2021/142460
§ 371 (c)(1),
(2) Date: Jul. 14, 2023

(87) PCT Pub. No.: WO2022/151978
PCT Pub. Date: Jul. 21, 2022

(65) Prior Publication Data

US 2024/0115645 A1 Apr. 11, 2024

(30) Foreign Application Priority Data

Jan. 18, 2021 (CN) ......................... 202110060462.2

(51) Int. Cl.
*A61K 36/69* (2006.01)
*A61K 31/7048* (2006.01)
*A61P 13/12* (2006.01)

(52) U.S. Cl.
CPC .......... *A61K 36/69* (2013.01); *A61K 31/7048* (2013.01); *A61P 13/12* (2018.01); *A61K 2236/13* (2013.01); *A61K 2236/15* (2013.01); *A61K 2236/331* (2013.01); *A61K 2236/333* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| | | |
|---|---|---|
| CN | 1653929 A | 8/2005 |
| CN | 1907340 A | 2/2007 |

(Continued)

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*

Ghodasara, J., Pawar, A., Deshmukh, C., & Kuchekar, B. (2010). Inhibitory effect of rutin and curcumin on experimentally-induced calcium oxalate urolithiasis in rats. Pharmacognosy Research, 2(6), 388. (Year: 2010).*

Wu J., "Studies on the Chemical Constituents and Biological Activities from Two Medicinal Plants of Polygala", Shenyang Pharmaceutical University Doctorel Thesis (200 pages) (Jun. 2007), together with an English-language translation of p. 17.

(Continued)

*Primary Examiner* — Dale R Miller
(74) *Attorney, Agent, or Firm* — Scully, Scott, Murphy & Presser, P.C.

(57) ABSTRACT

Provided in the present invention is a pharmaceutically active ingredient extract extracted from *Polygala japonica* Houtt., which extract comprises a flavonol compound of the following formula (I) structure as a first active ingredient, and optionally comprises a xanthone compound selected from the following formula (II) as a second active ingredient and a glycolipid compound selected from the following formula (III-1) as a third active ingredient. An animal experiment confirms that the drug of the present invention has significantly better effects than potassium sodium hydrogen citrate in typical test indicators such as calcium oxalate crystal aggregation, renal interstitial inflammatory cell infiltration and renal tubule dilation lesions, showing that the drug has high potential and market prospects in the treatment of urolithiasis and urinary tract infections or kidney damage caused by urolithiasis, and as an adjuvant drug after surgical treatment of urolithiasis.

(I)

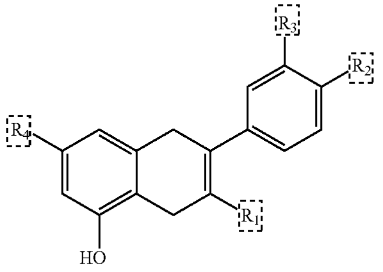

(II)

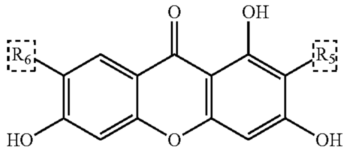

(III)

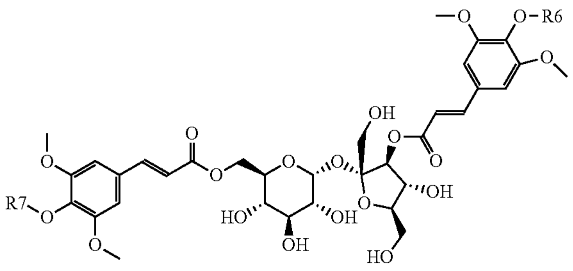

7 Claims, 8 Drawing Sheets
(8 of 8 Drawing Sheet(s) Filed in Color)

(56) References Cited

FOREIGN PATENT DOCUMENTS

| | | | | | |
|---|---|---|---|---|---|
| CN | 1303097 | C | | 3/2007 | |
| CN | 1931228 | A | | 3/2007 | |
| CN | 102068627 | A | | 5/2011 | |
| CN | 102503924 | A | | 6/2012 | |
| CN | 103285355 | A | | 9/2013 | |
| CN | 103432196 | A | * | 12/2013 | ............ A61K 36/53 |
| CN | 103704591 | A | | 4/2014 | |
| CN | 103006793 | B | | 7/2014 | |
| CN | 104083644 | A | | 10/2014 | |
| CN | 105213919 | A | | 1/2016 | |
| CN | 104004110 | B | | 3/2016 | |
| CN | 105943975 | A | * | 9/2016 | ............ A61K 47/26 |
| CN | 105998861 | A | | 10/2016 | |
| CN | 108159126 | A | | 6/2018 | |
| CN | 108948125 | A | | 12/2018 | |
| CN | 111419909 | A | | 7/2020 | |
| CN | 114031656 | A | | 2/2022 | |
| WO | WO-2020204848 | A1 | * | 10/2020 | ............ A61K 36/26 |

OTHER PUBLICATIONS

Kim Y-J et al., “Beauty Food Activities of Polygala Japonica Houtt”, J Appl Biol Chem 61(1): 51-57 (2018) (cited in JP OA).

Tizziani T. et al., “Phytochemical and Chemotaxonomic Study of Polygala Altomontana (Polygalaceae)”, Biochemical Systematics and Ecology 77:1-2 (2018) (cited in JP OA).

Kou J. et al., “Antiinflammatory Activity of Polygala Japonica Extract”, Fitoterapia 77:411-415 (2006) (cited in JP OA).

Cai, S. et al. (editors), “Atlast of Zhangzhou Commonly Used Chinese Herbal Medicine”, Fujian Science and Technology Publishing House, p. 139 (Mar. 2020), together with an English-language translation (cited in CN OA & SR.).

International Search Report dated Mar. 18, 2022 issued in PCT/CN2021/142460.

Ozbek, Hilal et al., “Trinorguaian and germacradiene type sesquiterpenes along with flavonoids from the herbs of Pimpinella cappadocica Boiss. & Bal.” Phytochemistry Letter (Dec. 4, 2014), vol. II, pp. 74-79.

Haraguchi, Mitsue et al., “Triterpenoid saponins and flavonol glycosides from Phytolacca thyrsiflora” Phytochemistry (Dec. 31, 1988), vol. 27, No. 7, pp. 2291-2296.

Li, T.-Z. et al. “New flavonol glycosides and new xanthone from Polygala Japonica”, Journal of Asian Natural Products Research (Aug. 31, 2006), vol. 8, No. 5, pp. 401-409.

Zhang, Jingjing et al., “Advances on Chemical Constituents and Pharmacological Activities of Poly gala japonica Houtt”, Modern Chinese Medicine (Nov. 30, 2015), vol. 17, No. 11, pp. 1216-1222.

Li, Tinzhao, “Bio-Assay Guided Isolation of the Anti-Depressive Constituents of Polygala Japonica Houtt. & Studies on the Active Constituents of Patrinia Scabra”, Chinese Doctoral Dissertations & Master’s Theses Full-text Database (Doctor), Medicine & Public Health, Oct. 15, 2005, pp. 12-15.

Wu, Jianfeng et al., “Studies on the Chemical Constituents and Biological Activities from Two Medicinal Plants of Polygala)”, Chinese Doctoral Dissertations & Master’s Theses Full-text Database (Doctor), Medicine & Public Health (Nov. 15, 2007).

Jiang, Yong et al., “Xanthone Glycosides from Polygala tenuifolia and Their Conformational Analyses”, Journal of Natural Products (May 19, 2005), vol. 68, No. 6, pp. 875-879.

Dong, Meiyue et al., “Chemical constituents from the seeds of *Raphanus sativus* L. and their chemotaxonomic significance”, Biochemical Systematics and Ecology (Sep. 8, 2020), vol. 93, p. 104138.

Zhao, Xin et al., “UHPLC-MS/MS method for pharmacokinetic and bioavailability determination of five bioactive components in raw and various processed products of Polygala tenuifolia in rat plasma”, Pharmaceutical Biology (Sep. 21, 2020), vol. 58, No. 1, pp. 969-978.

Goda, Yukihiro et al., “Constituents in watercress: inhibitors of histamine release from RBL-2H3 cells induced by antigen stimulation”, Biological & Pharmaceutical Bulletin (Dec 31, 1999), vol. 22, No. 12, pp. 1319-1326.

Majumder, Ranabir et al., “Screening of plant-based natural compounds as a potential COVID-19 main protease Inhibitor: an in silico docking and molecular dynamics simulation approach”, Journal of Biomolecular Structure and Dynamics (Sep. 8, 2020), vol. 40, No. 2, pp. 696-711.

Li, Wenkui et al., “A Study on Chemical Constituents of Polygala Japonica”, Natural Product Research and Development (Sep. 30, 1996) vol. 8, No. 3, pp. 1-4.

“Chinese Pharmacopoeia”, 2015 edition, vol. 1.

* cited by examiner

DRUG FOR TREATING UROLITHIASIS-RELATED DISEASE, AND PREPARATION METHOD THEREFOR

CROSS-REFERENCE TO RELATED APPLICATIONS

The present application claims priority to Chinese Patent Application No. 202110060462.2 filed on Jan. 18, 2021, the content of which is incorporated by reference in its entirety herein.

FIELD OF THE INVENTION

The present invention belongs to the field of pharmaceutical chemistry. Specifically, the present invention provides a drug for treating urolithiasis, the drug is a plant *Polygala japonica* Houtt. extract comprising structurally specific flavonol compounds, xanthones and glycolipids as main active ingredients; wherein the extract is preferably the extract from the stem and leaf part of *Polygala japonica* Houtt. The drug of the present invention is obviously superior to the existing mainstream clinical drug potassium sodium hydrogen citrate and has less side effects in the treatment of urolithiasis and urinary tract infections or kidney damage caused by urolithiasis and as an adjuvant drug after surgical treatment of urolithiasis, and thus has good medical economic value.

BACKGROUND OF THE INVENTION

Urolithiasis (referred to as urinary calculus) is the disease earliestly discovered by humans. Urinary calculus was found in the tomb of El Amrah in Egypt as early as 4800 BC, 6800 years ago. More than 2,000 years ago, Hippocrates noted that nephrapostasis caused by renal calculus, and also described arthrolithiasis. There are also described for urolithiasis and urolithic stranguria in ancient medical books in two thousand years ago in China. Urolithiasis is not only a disease of humans, but also occurs in animals.

Urolithiasis is a general term for diseases caused by urinary calculus, which is formed by the precipitation and condensation of crystals in urine. The pathogenesis of urolithiasis is related to the presence of factors in the urine that promote calculus-forming salts supersaturation (eg, excess excretion of salts, urine acidity, decreased urine output), preformed cores (eg, uric acid crystals and other calculus), and abnormal inhibitors of crystallization formation. Idiopathic hypercalciuria [urinary calcium >300 mg/d (>7.5 mmol/d) in men, and >250 mg/d (6.2 mmol/d) in women], a hereditary disease, occurs in 50% of men with calcium calculus and 75% of women with calcium calculus. Hypocitraturia [urinary citric acid <350 mg/d (<1820 μmol/d)] alone or in combination with other diseases can promote formation of calculus because citric acid normally binds urinary calcium to form soluble calcium citrate.

There are many areas with a high incidence of urinary calculus in the world, called calculus areas, which mainly refer to areas with a high incidence of malnutrition and vesical calculus in children. Areas with a relatively high incidence of urinary calculus are the Southeastern United States, the United Kingdom, the Nordic countries, the Mediterranean countries, the Northern India, Pakistan, the Northern Australia, the Central Europe, the Malay Peninsula, the Southern China, and so on. The areas with low incidence are Central and South America, Africa, and so on. The average incidence of urolithiasis in China is 5%, and there are about 50 million patients with urolithiasis. The distribution has a certain area distribution. The incidence is relatively high in areas such as Guangdong, Guangxi, Yunnan, Guizhou, Shandong, Hunan, Jiangxi and Anhui provinces. The incidence in the South is significantly higher than that in the North. The lowest incidence is 2.5% in Heilongjiang, and the highest incidence is 59% in Guizhou, a difference of 20 times. Moreover, the recurrence rate of urolithiasis is very high, about 15 to 50%.

For a long time, people have been exploring effective treatment methods for urolithiasis, including extracorporeal shock wave lithotripsy, flexible ureteroscopy lithotripsy, minimally invasive percutaneous nephrolithotomy, (calculus diameter ≤2 cm), open operation (calculus diameter ≥2 cm), drug treatment (calculus diameter <0.6 cm) and other methods. Among them, extracorporeal shock wave lithotripsy for calculus at the upper, middle, and lower narrow ureteral openings will inevitably cause ureteral injury, and impacting calculus at the renal pelvis may also cause kidney injury, and clinically hematuria is obvious. Lithotripsy and calculus removal by flexible ureteroscopy can also cause damage to the ureter and kidney, which may result in incomplete calculus removal. Lithotripsy and calculus removal by minimally invasive percutaneous nephrolithotomy will lead to kidney damage and incomplete calculus removal. With the development of clinical medicine, open operation is rarely used to treat renal calculus.

Clinically, excretion-promoting agents such as potassium sodium hydrogen citrate granules, potassium citrate, thiazide diuretics, magnesium, and acetylcysteine are commonly used as western medicine for the treatment of urolithiasis, but their effects are not ideal, and the toxic and side effects are obvious. Potassium sodium hydrogen citrate granules (trade name: Uralyt-U) are the first citrate preparations in the world to successfully dissolve and prevent uric acid calculus developed by MADAUS AG in Germany in 1965. In 2005, it was recommended by the Urolithology Group of the Urology Branch of the Chinese Medical Association as the only legal domestic citrate preparation with independent chemical structure and calculus-dissolving effect. However, potassium sodium hydrogen citrate granules need to be ingested in a very high effective dose, and the daily dose is 4 bags (each bag is 2.5 grams, a total of 10 grams of granules), taken three times after meals. Take one bag each in the morning and noon, and take two bags at night. The granules can be taken with water. One gram of potassium sodium hydrogen citrate contains 0.172 grams or 4.4 mmol of potassium and contains 0.1 grams or 4.4 mmol of sodium (equivalent to 0.26 grams of sodium chloride). Taking such a large amount of sodium and potassium ions every day can cause serious diseases such as severe hyperkalemia, cardiac arrhythmia, and hypertension, thus severely limiting the scope of use of this drug.

In China, a large number of Chinese herbal medicine and Chinese patent medicine as therapeutic regimens have also been explored in clinical and medical research. For example, Chinese patent applications CN103285355A, CN103704591A, CN104083644A, CN105213919A, CN105998861A, CN1653929A and the like, have described a series of multi-composition' Chinese herbal medicines for treating urolithiasis. However, multi-composition Chinese herbal medicines generally have problems such as complex ingredients, primitive pharmaceutical technology, difficult quality control, inaccurate quantitative detection methods, large dosage, imperfect quality control standards, and failure to meet modern clinical pharmaceutical standards and medication requirements. In addition, some traditional Chinese patent medicines such as Bishitong, Paishi Granules, Shilintong Tablets, and Relinqing Granules are also common Chinese patent medicines used to treat urolithiasis. However, these traditional Chinese patent medicines have problems such as complex ingredients, primitive pharmaceutical technology, difficult quality control, inaccurate quantitative detection methods, large dosage, and imperfect quality control standards, and failure to meet the modern clinical medication requirements.

With the continuous deepening of the reform of Chinese drug evaluation system, the quality requirements for the drugs declared for registration continue to increase. Among them, for clinical trials of Chinese herbal medicines and their active extracts, the new approval standards generally require a double-blind comparative trial compared with typical western medicines for the same indication (such as potassium sodium hydrogen citrate for the treatment of urolithiasis), and it is required that only when natural medicines or their extracts achieve the same or better clinical efficacy and safety as western medicines (compound medicines) with the same indication in clinical trials, the natural medicines or their extracts may be approved for marketing. Due to the high requirements of the evaluation standards for natural medicines, there are currently 40-50 marketing authorizations for chemical and biological new drugs in China every year, but only 1-2 marketing authorizations for traditional Chinese medicines or natural medicines each year. Therefore, although there are pharmaceutical companies trying to extract effective active extracts and effective active ingredients from various Chinese herbal medicines for the treatment of urolithiasis in recent years, almost none of them have obtained marketing authorization. Even individual drugs that entered Phase II/III clinical trials still failed in the end. An important reason is that the research on the active parts and active ingredients of these drugs is insufficient, resulting in the clinical effectiveness and safety of these drugs being significantly inferior to existing typical clinical western medicines such as potassium sodium hydrogen citrate, so they failed to pass the evaluation and obtain marketing authorization.

Therefore, the development of drugs for urolithiasis with low cost, simple process, safe and effective, stable and controllable quality, clear curative effect, less side effects (equivalent to or better than the existing mainstream drug for urolithiasis, potassium sodium hydrogen citrate), better absorption in the body, and meeting modern drug registration requirements, are still an urgent pursuit of the medical community.

*Polygala japonica* Houtt. is a plant from Polygalaceae, which is widely distributed in China. It has been widely used as folk medicine in China, mainly for eliminating phlegm and relieving cough, dissipating blood stasis and hemostasis, calming the mind and calming the nerves, detoxifying and reducing swelling.

The functions and indications of the traditional Chinese medicine *Polygala japonica* Houtt. described in "Chinese Pharmacopoeia" (2015 edition, Volume 1) are to eliminate phlegm and relieve cough, promote blood circulation and reduce swelling, detoxify and relieve pain. Used for cough with excess phlegm, sore throat; external treatment of bruises, boils, furuncles, and snake bites.

The preparation of *Polygala japonica* Houtt. described in "Chinese Pharmacopoeia" (2015 edition, Volume 1) is the compound *Polygala japonica* Houtt. granules, and the prescription is: *Polygala japonica* Houtt. 150 g, Folium Isatidis 350 g, Wild Chrysanthemum 200 g, Spora Lygodii 250 g, Herba Hedyotis 250 g, Herba Violae 200 g. Functions and indications: clearing away heat and relieving sore throat, dispelling stagnation and relieving pain, eliminating phlegm and relieving cough. It is used for pharyngeal swelling, sore throat, fever, and cough caused by wind-heat attacking the lung or phlegm-heat obstructing the lung; acute pharyngitis, acute exacerbation of chronic pharyngitis, and upper respiratory tract infection see the above syndromes.

In addition, there are also a large number of patent documents that describe the extraction of various active ingredients of *Polygala japonica* Houtt, for pharmaceutical uses. For example, the patent CN1303097C describes the polygalae saponins and their aglycones, total saponins and their total aglycones, and their effects in treating depression, intelligence development, sedation, anti-anxiety and hypnosis. The patent CN104004110B describes the application of the polygala *japonica* polysaccharide extracted from polygala *japonica* in the preparation of drugs and health food for enhancing the immune function of the body. The patent CN108159126A describes the application of a polygalasaponin extract in preparing an antitumor drug. The patent CN103006793B describes a separation and purification process for effective anti-inflammatory parts of Japanese polygala, and discloses that the total flavonoids and total saponin extracts of Japanese polygala are the anti-inflammatory effective parts. The patent CN108948125A, method for preparing Japanese milkwort herb sapogenin by utilizing Japanese milkwort herb, mentions the method of preparing Japanese milkwort herb sapogenin and the method of preparing Japanese milkwort herb flavones, which mentions four specific flavone molecules: kaempferol-3-O-6"-O-(3-hydroxy-3-methyl-glutaryl) glucoside, astragulin, kaempferol 3-(6-acetyl) glucoside, kaempferol 3,7-diglucoside. However, the pharmaceutical activity of the extracted components has not been confirmed. Moreover, the existing published documents do not disclose the use of the specific extract of *Polygala japonica* Houtt, for the treatment of urolithiasis.

In addition, the above-mentioned patents all use the whole herb of *Polygala japonica* Houtt., and use saponin compounds as indispensable active ingredients. The quality control detection standard for the compound of *Polygala japonica* Houtt. described in "Chinese Pharmacopoeia" (2015 edition, Volume 1) is: the content of *Polygala japonica* Houtt. saponin (C53H86023) should not be less than 0.60%, calculated as a dry product. However, the chemical components of *Polygala japonica* Houtt. include saponins, flavonoids, glycolipids, alkaloids, phenols, tannins, polysaccharides, etc., and the components are very complex. According to CNKI literature search, there are more than 100 kinds of compounds with confirmed molecular structures. Therefore, it is difficult to develop the whole herb of *Polygala japonica* Houtt. into a natural medicine that meets modern pharmaceutical standards. In fact, only the compound preparations of *Polygala japonica* Houtt. are currently on the market, and even *Polygala japonica* Houtt. used as a single Chinese herbal medicine is not on the market.

SUMMARY OF THE INVENTION

The main purpose of the present invention is to provide a drug for urolithiasis with low cost, simple process, safe and effective, stable and controllable quality, clear curative effect, less side effects (equivalent to or better than the existing mainstream drug for urolithiasis, potassium sodium hydrogen citrate), better absorption in the body, and meeting modern drug registration requirements.

Through a lot of experimental research, the inventors find the pharmaceutically active ingredient extract of flavonol compounds with a specific structure of formula (I) extracted from the plant *Polygala japonica Houtt.*

Specifically, the present invention provides a pharmaceutically active ingredient extract extracted from the plant *Polygala japonica* Houtt., the extract comprises a flavonol compound of the following formula (I) as a first active ingredient, (I)

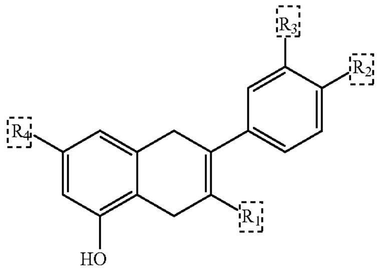

wherein, $R_1$ is selected from the group consisting of —OH, —O-Glc, —O-Gal, —O-Api, -ORha, —O-Glc-Glc, —O-Glc-Gal, —O-Glc-Api, —O-Glc-Rha, —O-Gal-Glc, —O-Gal-Gal, —O-Gal-Api, —O-Gal-Rha, —O-Glc-Glc-Api, —O-Gal-Glc-Api, -Q-Glc-Gal-Api, —O-Gal-Gal-Api, —O-Gal-Rha-Gal, —O-Gal-Rha-Glc, —O-Glc-Rha-Glc, and —O-Glc-Rha-Gal;

$R_2$ is a substituent selected from the group consisting of —OH, —O-Me, —O-Glc, —O-Gal, —O-Api, and —O-Rha;

$R_3$ is a substituent selected from the group consisting of H, OH, —O-Me, —O-Glc, —O-Gal, —O-Api, and —O-Rha;

$R_4$ is a substituent selected from the group consisting of OH, and —O-Me;

The pharmaceutically active ingredient extract optionally comprises a xanthone compound selected from the following formula (II) as a second active ingredient, and a glycolipid compound selected from the following formula (III) as a third active ingredient (II)

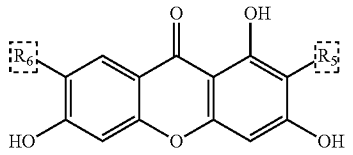

wherein, $R_5$ is a substituent selected from the group consisting of —O-Gal, —O-Api, -ORha, —O-Glc-Glc, —O-Glc-Gal, —O-Glc-Api, —O-Glc-Rha, —O-Gal-Glc, —O-Gal-Gal, —O-Gal-Api, —O-Gal-Rha, —O-Api-Glc, —O-Api-Gal, —O-Api-Api, and —O-Api-Rha; $R_6$ is a substituent selected from the group consisting of —OH, and —O-Me;

(III)

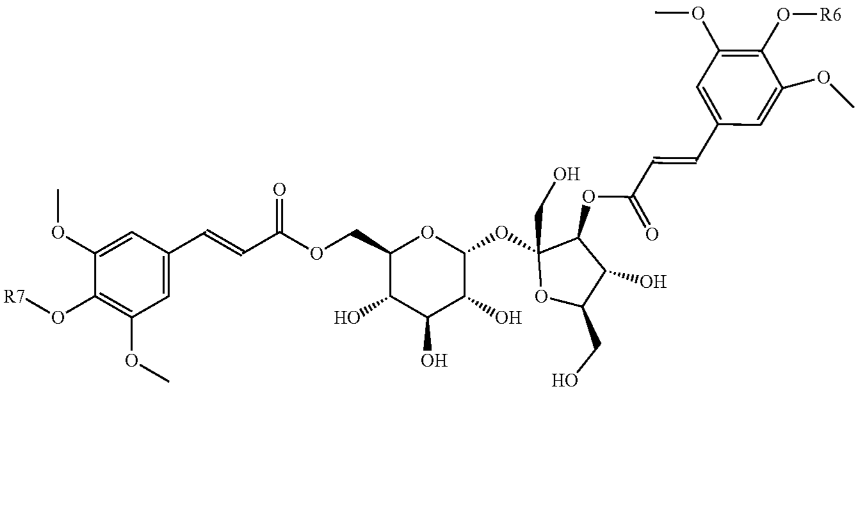

wherein, $R_7$, $R_8$ are each independently selected from the group consisting of H, and CH3; and wherein, in the definition of $R_1$-$R_6$ in the above formula (I) and formula (II), Glc represents glucosyl, Gal represents galactosyl, Api represents celosyl, and Rha represents rhamnose.

In a preferred technical solution, the flavonol compound of formula (I) as the first active ingredient is preferably selected from one or more of the compounds of the following general formula (F-7K)

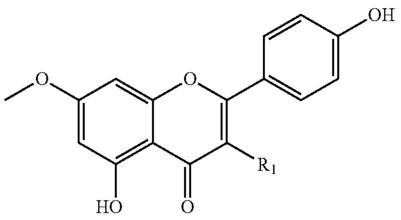

wherein, $R_1$ is selected from the group consisting of —OH, —O-Glc, —O-Gal, —O-Glc-Glc, —O-Glc-Gal, —O-Glc-Rha, —O-Gal-Glc, —O-Gal-Gal, —O-Gal-Rha, —O-Glc-Glc-Api, —O-Gal-Glc-Api, —O-Glc-Gal-Api, and —O-Gal-Gal-Api, (F-7Q)

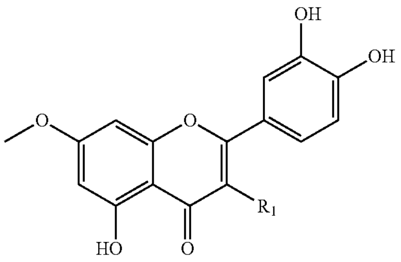

wherein, $R_1$ is selected from the group consisting of —OH, —O-Glc, —O-Gal, —O-Glc-Glc, —O-Glc-Gal, —O-Glc-Api, —O-Glc-Rha, —O-Gal-Glc, —O-Gal-Gal, —O-Gal-Api, —O-Gal-Rha, —O-Glc-Glc-Api, —O-Gal-Glc-Api, —O-Glc-Gal-Api, —O-Gal-Gal-Api, —O-Gal-Rha-Gal, —O-Gal-Rha-Glc, —O-Glc-Rha-Glc, and —O-Glc-Rha-Gal, (F-74Q)

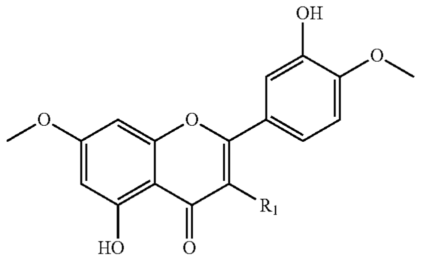

wherein, $R_1$ is selected from the group consisting of —OH, —O-Glc, —O-Gal, —O-Glc-Api, —O-Gal-Api, (F-K)

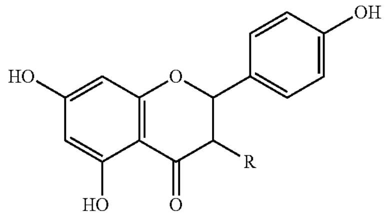

wherein,

R is selected from the group consisting of —OH, —O-Glc, —O-Gal, —O-Glc-Rha, and —O-Gal-Rha, (F-Q)

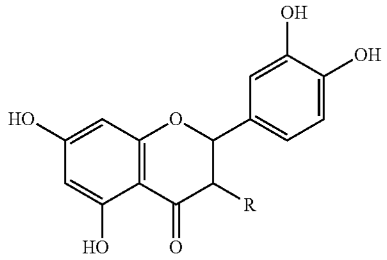

wherein,

R is selected from the group consisting of —OH, —O-Glc, —O-Gal, —O-Glc-Rha, and —O-Gal-Rha, (F-74K)

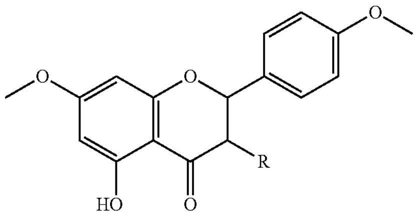

wherein,

R is selected from the group consisting of —OH, —O-Gal, and —O-Gal-Api;

The xanthone compound of formula (II) as the second active ingredient is preferably selected from one or more of the following formulas (II-1), (III-2) and (II-3)

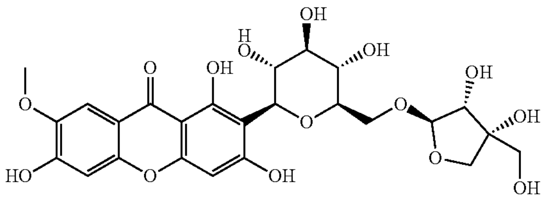 [SMILES: COc1cc2c(=O)c3c(O)c([C@@H]4O[C@H](CO[C@@H]5OC[C@](O)(CO)[C@H]5O)[C@@H](O)[C@H](O)[C@H]4O)c(O)cc3oc2cc1O]

(II-1, polygalaxanthone III)

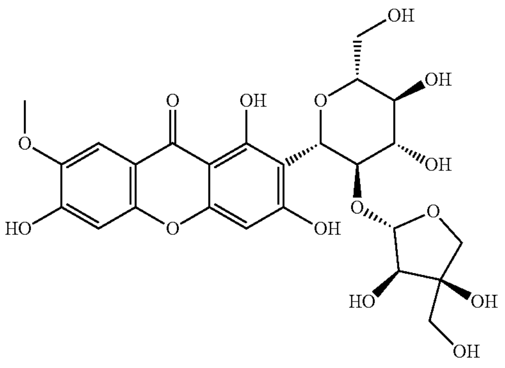 [SMILES: COc1cc2c(=O)c3c(O)c([C@@H]4O[C@H](CO)[C@@H](O)[C@H](O)[C@H]4O[C@@H]4OC[C@](O)(CO)[C@H]4O)c(O)cc3oc2cc1O]

(II-2, polygalaxanthone XI)

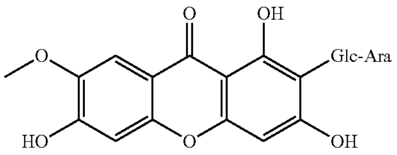

(II-3, polygalaxanthone VIII)

The glycolipid compound as the third active ingredient is preferably a compound of the following formula (III-1) or (III-2):

In a further preferred technical solution, the first active ingredient in the pharmaceutically active ingredient extract of *Polygala japonica* Houtt. is selected from the flavonol compounds of the above general formulas F-7K, F-7Q, F-74Q, and F-74K.

In a further preferred technical solution, the first active ingredient in the pharmaceutically active ingredient extract of *Polygala japonica* Houtt. is preferably at least one selected from the following compounds:

(F-7Q-1)

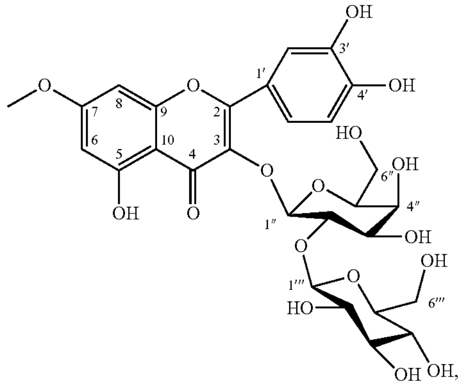

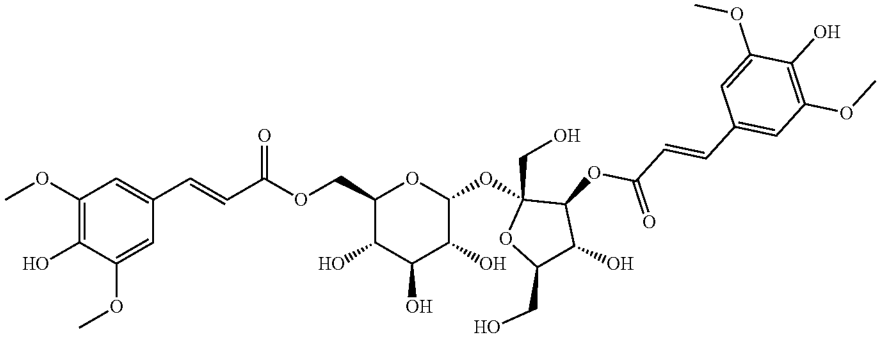

(III-1, 3,6'-disinapoyl sucrose)

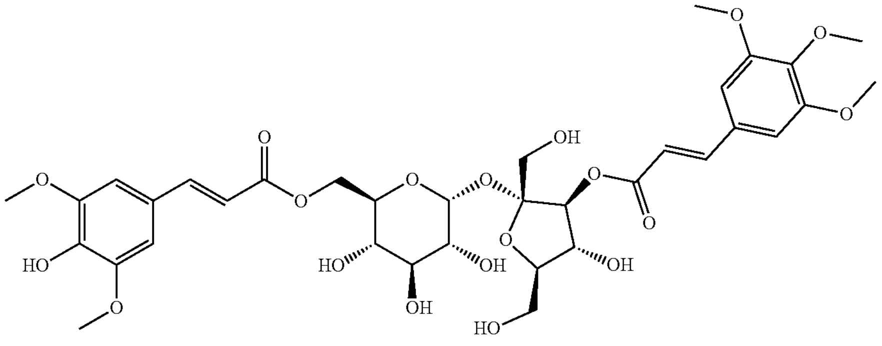

(III-2, Tenuifoliside C).

-continued (F-7K-1)

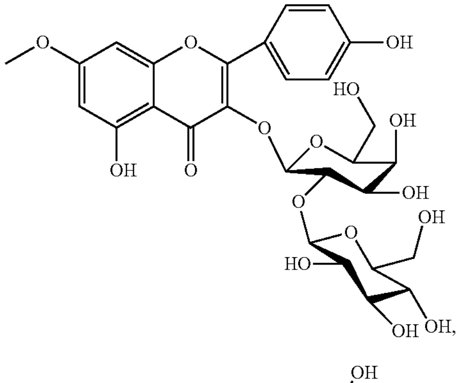

(F-74Q-1)

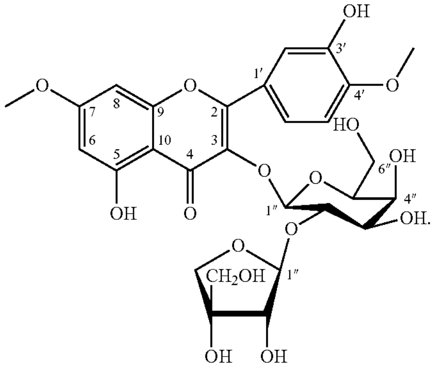

In a further preferred technical solution, in the pharmaceutically active ingredient extract of *Polygala japonica* Houtt., the total content of the flavonol compound of the formula (I) as the first active ingredient, and optionally the xanthone of the formula (II) as the second active ingredient and the glycolipid of formula (III) accounts for 30-100% of the total extract of *Polygala japonica* Houtt., wherein, the component content (%) is the HPLC % content calculated by using the HPLC integral area normalization method according to the common method in the art.

In a further preferred technical solution, in the pharmaceutically active ingredient extract of *Polygala japonica* Houtt., the total content of the flavonol compound of formula (I) as the first active ingredient accounts for 20-100% of the total extract of *Polygala japonica* Houtt.

In a further preferred technical solution, in the pharmaceutically active ingredient extract of *Polygala japonica* Houtt., the total content of the flavonol compound of formula (I) as the first active ingredient accounts for 75-100% of the total extract of *Polygala japonica* Houtt.

The present invention also provides a method for preparing the pharmaceutically active ingredient extract of *Polygala japonica* Houtt., comprising the following steps (1) Pretreatment of *Polygala japonica* Houtt.

The raw material of *Polygala japonica* Houtt. is obtained by taking the whole herb of *Polygala japonica* Houtt, or the aboveground part of *Polygala japonica* Houtt., or commercially available pharmaceutical materials of *Polygala japonica* Houtt., washing and crushing;

(2) Rough Extraction of Effective Parts of *Polygala japonica* Houtt.

The total alcohol extract of *Polygala japonica* Houtt. is obtained by taking some of the raw material of *Polygala japonica* Houtt. obtained in step (1), heating and refluxing with ethanol with a concentration of 20-95% (v/v) that is about 6 to 12 times the weight of the raw material of *Polygala japonica* Houtt, for 1 to 3 hours each time, and repeatedly refluxing to extract 1 to 3 times, combining the obtained alcohol extract, filtering or centrifuging, and concentrating;

or, the total water extract of *Polygala japonica* Houtt. is obtained by taking some of the raw material of *Polygala japonica* Houtt. obtained in step (1), heating them to boil with deionized water about 6 to 15 times the weight of *Polygala japonica* Houtt, and keeping boiling for 1 to 3 hours, repeatedly extracting for 1 to 3 times, combining the obtained water extract, filtering or centrifuging, and concentrating;

(3) Refining of Effective Parts of *Polygala japonica* Houtt.

The required pharmaceutically active ingredient extract of *Polygala japonica* Houtt. is obtained by separating the total water extract or total alcohol extract concentrate of *Polygala japonica* Houtt. in step (2) with a macroporous adsorption resin or polyamide resin chromatographic column, and sequentially gradient eluting with different ratios of water/ethanol until the eluent is colorless, collecting the 0-95% ethanol gradient eluent, and drying under reduced pressure.

In the above extraction method, it is preferred that in the step (3), the macroporous resin is selected from type D101, type HPD100, type HPD200 or type AB-8 macroporous resin, and the polyamide resin is selected from 100-200 mesh SCR polyamide resin.

In the above-mentioned extraction method, it is preferred that in the step (1), *Polygala japonica* Houtt. is preferably the stem and leaf part of *Polygala japonica* Houtt.

In the above extraction method, it is preferred that in the step (3), the macroporous resin is selected from type D101 or type AB-8 macroporous resin, and the polyamide resin is selected from 100-200 mesh SCR polyamide resin.

In the above extraction method, it is preferred that in the step (3), the gradient eluting is performed by sequentially eluting with water, 25% ethanol, 50% ethanol, 75% ethanol, and 95% ethanol until the eluent is colorless.

The present invention provides the use of the pharmaceutically active ingredient extract of *Polygala japonica* Houtt. in the preparation of medicament, and the medicament is used for treating or preventing urolithiasis and urinary tract infections or kidney damage caused by urolithiasis, and as an adjuvant drug after surgical treatment of urolithiasis.

The present invention also provides a pharmaceutical composition comprising at least one compound selected from the following formulas as an active ingredient:

(F-7Q-1)

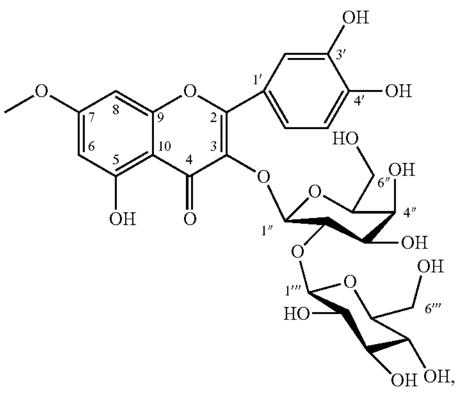

-continued (F-7K-1)

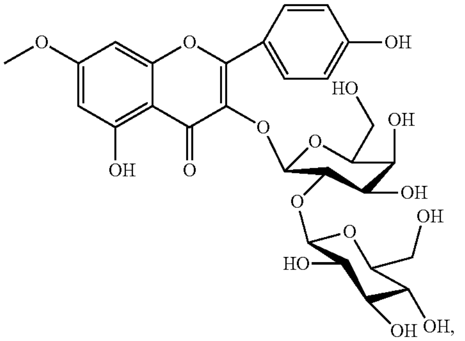

(F-74Q-1)

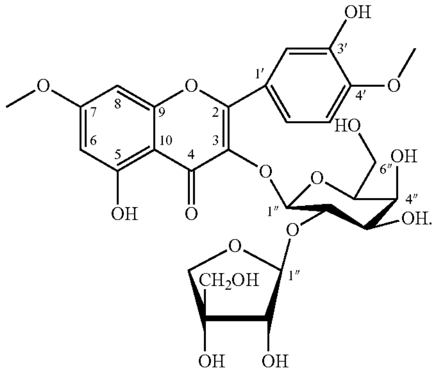

In a preferred technical solution, the pharmaceutical composition further comprises a pharmaceutically acceptable carrier, excipient or auxiliary material.

The present invention further provides the use of the above-mentioned pharmaceutical composition in the preparation of medicament, and the medicament is used for treating or preventing urolithiasis and urinary tract infections or kidney damage caused by urolithiasis, and as an adjuvant drug after surgical treatment of urolithiasis.

The present invention also provides the use of any one of the following compounds in the preparation of medicament, (F-7Q-1)

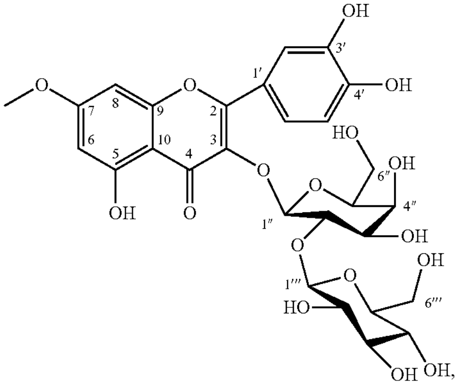

-continued (F-7K-1)

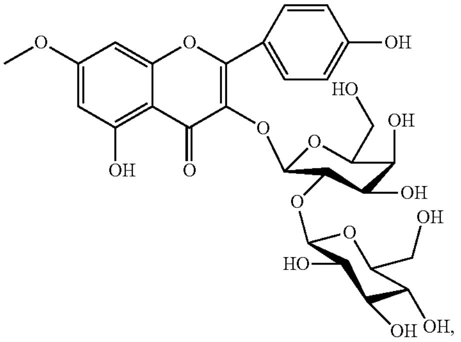

(F-74Q-1)

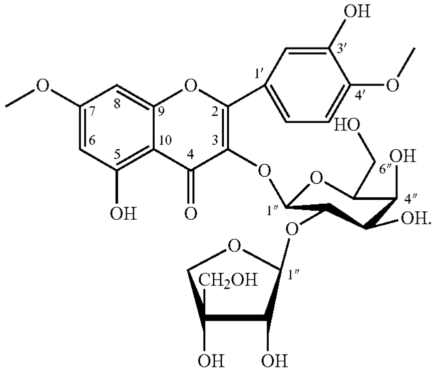

The medicament is used for treating or preventing urolithiasis and urinary tract infections or kidney damage caused by urolithiasis, and as an adjuvant drug after surgical treatment of urolithiasis.

The inventors found through a large number of experimental studies that the active ingredient extract of the present invention can be used in the treatment of urolithiasis and urinary tract infections or kidney damage caused by urolithiasis, and as an adjuvant drug after surgical treatment of urolithiasis, has significantly better effects than the Chinese herbal medicines and herbal medicine extracts described in the currently known published literature, and has an effect equivalent to or better than that of the known clinical western medicine potassium sodium hydrogen citrate (for details, see the following pharmacological examples). Preliminary study shows that the key is that the compounds of formula (I) and formula (II) selected as the main active ingredients in the present invention have a hydroxyl group as a substituent at the β position of the carbonyl in the flavonoids and xanthones, wherein the hydroxyl group and the ketone carbonyl group act together to more effectively react with calcium ion-containing components of the calculus in the urinary system, thereby more effectively degrading or dissolving the calculus in the urinary system.

Therefore, in a specific technical solution of the present invention, the use of any one of the aforementioned compounds of formula (I), formula (II), or a combination of two or more thereof in the preparation of medicament is provided. The medicament is used for treating or preventing urolithiasis and urinary tract infections or kidney damage caused by urolithiasis, and as an adjuvant drug after surgical treatment of urolithiasis.

In a preferred technical solution of the present invention, any one of the aforementioned compounds of formulas (I-1) to (I-4), and/or formulas (II-1) to (II-3), or a combination of two or more thereof in the preparation of medicament is provided. The medicament is used for treating or preventing urolithiasis and urinary tract infections or kidney damage caused by urolithiasis, and as an adjuvant drug after surgical treatment of urolithiasis.

The pharmaceutically active ingredient extract of *Polygala japonica* Houtt. of the present invention can also be prepared into various dosage forms by conventional methods of pharmacy, such as gastrointestinal administration dosage forms such as capsules, tablets, pills, oral liquids, granules, tinctures, sustained release agents, and parenteral dosage forms such as injections and external preparations.

DESCRIPTION OF THE FIGURES

The patent or application file contains at least one drawing executed in color. Copies of this paper or patent application publication with color drawing(s) will be provided by the Office upon request and payment of the necessary fee.

DETAILED DESCRIPTION OF THE INVENTION

Figure 1:
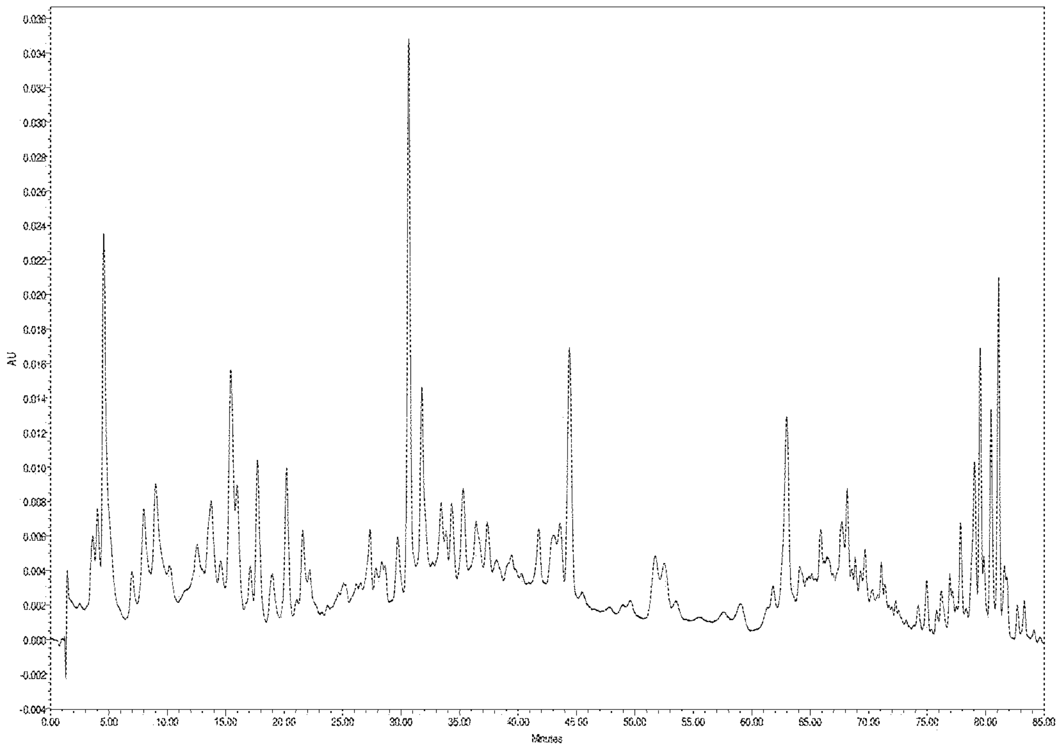
FIG. 1 is the HPLC analysis chromatogram of the alcohol extract from the whole herb of *Polygala japonica* Houtt. of the present invention.

Examples of the present invention are described in detail below, and the illustration of Examples is shown in the accompanying drawings. The Examples described below by referring to the drawings are exemplary only for explaining the present invention and should not be construed as limiting the present invention.

I. Preparation Examples

Preparation Example 1: Components Analysis of Alcohol Extract from the Whole Herb of *Polygala japonica* Houtt The whole herb of *Polygala japonica* Houtt. was weighed, in which 10 times the amount of 75% ethanol was added, the obtained solution was heated to reflux, extracted 3 times with each time for 3 hours, filtered while hot, and then the alcohol extracts were combined;

The alcohol extract was concentrated to an extract concentrate with a relative density of 1.1-1.3 g/ml.

The fingerprint analysis was performed for the obtained alcohol extract concentrate of *Polygala japonica* Houtt. by using HPLC.

HPLC test conditions: Mobile phase: acetonitrile (A), 0.1% formic acid aqueous solution (B), binary gradient separation;

Flow rate: 0.8 mL min-1;

Detection wavelength: 330 nm;

Column temperature: 20° C.;

Injection volume: 20 μL.

Chromatogram was recorded for 90 min.

Preparation Example 2: Components Analysis of Water Extract From the Whole Herb of *Polygala japonica* Houtt The whole herb of *Polygala japonica* Houtt. was weighed, in which 10 times the amount of deionized water was added, the obtained solution was heated to reflux, extracted twice with each time for 3 hours, filtered while hot, and then the water extracts were combined; the extract is a dark brown liquid.

The water extract was concentrated to an extract concentrate with a relative density of 1.1-1.3 g/ml.

The fingerprint analysis was performed for the obtained water extract concentrate of *Polygala japonica* Houtt. by using HPLC (see FIG. 1 of the accompanying drawings for details), and it can be basically confirmed that the extract mainly comprises dozens of compounds of four major types and dozens of compounds of other kinds. In the HPLC chromatogram, the peak time of xanthones is between 12-25 minutes, the peak time of flavonol compounds is between 18-68 minutes, the peak time of glycolipids is between 15-45 minutes, while the peak time of saponin is between 42-85 minutes.

Comparing the components obtained by the water extraction method and the alcohol extraction method, it can be found that: due to the relatively large polarity of water, the content of impurities with lower polarity such as chlorophyll in the extract obtained by the water extraction method will be less, whereas the high-polar tannin components will be more. The extract is dark brownish yellow. However, the content of low-polar components (such as chlorophyll, etc.) in the alcohol extract is more, while the content of high-polar components (such as tannin, etc.) is significantly reduced. The alcohol extract is greenish, but turns brownish yellow after cooling.

Whole herb extraction consumes a lot of pharmaceutical plants. Considering that most of the commercially available *Polygala japonica* Houtt. are the aboveground parts, it is also beneficial to protect the pharmaceutical plant resources by only selecting the aboveground parts and keeping the roots of the plants. Therefore, the inventor further tried to extract the active ingredient from the aboveground part of *Polygala japonica* Houtt. by alcohol extraction. The specific method is as follows.

Preparation Example 3: Components Analysis of Water Extract from the Aboveground Part of *Polygala japonica* Houtt The aboveground part of *Polygala japonica* Houtt. was weighed, in which 10 times the pharmaceutical material amount of deionized water was added, the obtained solution was heated to reflux, extracted 3 times with each time for 3 hours, filtered while hot, and then the water extracts were combined;

The water extract was concentrated to an extract concentrate with a relative density of 1.1-1.3 g/ml.

The fingerprint analysis was performed for the deionized water extract concentrate of the aboveground part of *Polygala japonica* Houtt. by using HPLC.

Preparation Example 4: Components Analysis of Alcohol Extract from the Aboveground Part of *Polygala japonica* Houtt The aboveground part of *Polygala japonica* Houtt. was weighed, in which 10 times the pharmaceutical material amount of 50% ethanol was added, the obtained solution was heated to reflux, extracted 3 times with each time for 3 hours, filtered while hot, and then the alcohol extracts were combined;

The alcohol extract was concentrated to an extract concentrate with a relative density of 1.1-1.3 g/ml.

Figure 2:
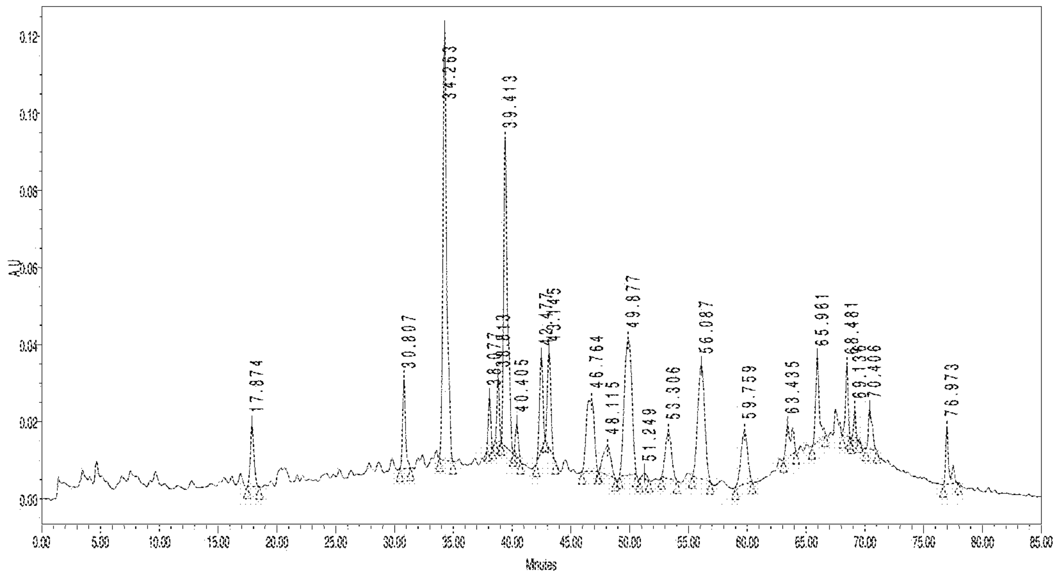
FIG. 2 is the HPLC analysis chromatogram of the alcohol extract from the aboveground part of *Polygala japonica* Houtt. of the present invention.

The fingerprint analysis was performed for the obtained alcohol extract concentrate of the aboveground part of *Polygala japonica* Houtt. by using HPLC (see FIG. 2 for the results).

In order to confirm the chemical composition of the extract concentrate, we analyzed it by HPLC-MS, in which MS analysis includes positive and negative ions and MS-MS, MS-MS-MS analysis, and compared the analysis results with the existing literatures, and preliminarily confirmed the structure types of four major categories of flavonol compounds, xanthones, glycolipids and saponins. Further, we subdivided flavonol compounds according to the differences in the parent core of flavonol compounds:

However, due to the complexity and diversity of the spatial structure and connection methods of glycosyls in glycosides, it can be determined whether the connection between multiple glycosides and the parent core of flavonol compounds is a single sugar chain, and the order of glycoside fragmentation in mass spectrometry through HPLC and multi-stage tandem MS, so as to confirm the molecular weight of the terminal sugar in the sugar chain and the basic type of glycogen. However, due to the complexity and diversity of the spatial structure and connection methods of glycosyls in glycosides, it needs to be further identified by other means for the configuration of the hydroxyl group on a certain carbon atom of the sugar ring of the isomer (such as glucose or galactose), the position of the sugar chain linkage between the glycoside and the glycoside (such as a 1-2 linkage, or a 1-4 linkage, or 1-6 linkage), and α or β configuration of the sugar configuration. Therefore, only through the structure identified by HPLC-MS-MS, compounds with the same molecular formula may have multiple structural combinations of aglycones in the flavonol compounds and different types of glycosides.

In order to facilitate the distinction, the present application uses the compound category to identify and distinguish the compounds that may have various combinations of structural units. For example, in the present application, F is used to represent the class of flavonol compounds, and F-Q represents a class of flavonol glycosides in which the parent core of the class of flavonol compounds is quercetin. In the structural determination, 302-162-132 represents that the parent core of aglycone in flavonol is quercetin, to which a glucose (or galactose) is connected, a celose is connected on this glucose (or galactose), wherein 302 is the parent core of quercetin, 162 is the molecular weight of the characteristic peak of glucose (or galactose) fragmentation fragments in mass spectrum, and 132 is the molecular weight of the characteristic peak of celose fragmentation fragments.

Through HPLC and multi-stage tandem MS analysis, it is preliminarily confirmed that the alcohol extract from the aboveground part of *Polygala japonica* Houtt. mainly comprises the following components:

TABLE 1

Component analysis of the alcohol extract from the aboveground parts of *Polygala japonica* Houtt.

| | Retention time HPLC/MS | Compound category | Molecular weight | Compound structure |
|---|---|---|---|---|
| 1 | 19.77 | F-Q | 596 | 302-162-132 |
| 2 | *20.344 | Xanthones | 568 | Xanthone III of *Polygala japonica* Houtt. |
| 3 | 21.867 | F-Q | 596 | 302-162-132 |
| 4 | 22.482 | F-Q | 464 | 302-162 |
| 5 | 24.080 | F-K | 580 | 286-162-132 |
| 6 | *30.807 | Glycolipids | 754 | Glycolipid (III-1) |
| 7 | 32.087 | F-7Q | 640 | 316-162-162 |
| 8 | *34.263 | F-7Q-1 | 640 | 316-162-162 |
| 9 | 38.077 | F-7K | 756 | 300-162-132-162 |
| 10 | 38.813 | F-7K | 756 | 300-162-132-162 |
| 11 | *39.413 | F-7K-1 | 624 | 300-162-162 |
| 12 | 40.405 | F-7Q | 610 | 316-162-132 |
| 13 | 42.477 | F-7Q | 478 | 316-162 |
| 14 | 43.145 | Saponins | 1120 | Saponin VIII of *Polygala japonica* Houtt. |
| 15 | *44.852 | Glycolipids | 768 | Glycolipid (III-2) |
| 16 | 46.718 | F-7K | 594 | 300-162-132 |
| 17 | 47.235 | F-7Q | 786 | 316-162-162-146 |
| 18 | 48.491 | F-74Q | 624 | 330-162-132 |
| 19 | 49.827 | F-7K | 462 | 300-162 |
| 20 | *49.877 | F-74Q-1 | 624 | 330-294(162 + 132) |
| 21 | 51.249 | Saponins | 1164 | Saponin |
| 22 | 53.306 | F-7K | 462 | 300-162 |
| 23 | 56.087 | F-74Q | 492 | 330-162 |
| 24 | 59.759 | F-7K | 770 | 300-162-162-146 |
| 25 | 62.343 | Saponins | 1398 | Saponin XXIX of *Polygala japonica* Houtt. |
| 26 | 63.435 | Saponins | 1252 | Saponin X of *Polygala japonica* Houtt. |
| 27 | *65.961 | F-74K-1 | 608 | 314-162-132 |
| 28 | 67.559 | Saponins | 1236 | Saponin |
| 29 | 68.042 | Saponins | 1104 | Saponin XXI of *Polygala japonica* Houtt. |

TABLE 1-continued

Component analysis of the alcohol extract from the aboveground parts of *Polygala japonica* Houtt.

| | Retention time HPLC/MS | Compound category | Molecular weight | Compound structure |
|---|---|---|---|---|
| 30 | 68.481 | Saponins | 872 | Saponin |
| 31 | 69.136 | Saponins | 1088 | Saponin |
| 32 | 70.406 | Saponins | 1220 | Saponin |
| 33 | 76.973 | Saponins | 710 | Saponin |

In the above table, the structure of the chemical composition mainly includes the following categories:

(1) Flavonols with Glycosides

1. A flavonol glycoside compound whose compound category is F-7K. Wherein, the aglycone structure of the compound is Rhamnocitrin with a molecular weight of 300 or 3,4',5-Trihydroxy-7-methoxyflavone, or 7-methoxyl-kaempferol, and the compound has the following general structure:

(F-7K)

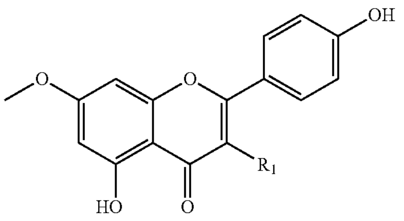

Wherein, $R_1$=glycosyl, which may be selected from the group consisting of —OH, —O-Glc, —O-Gal, —O-Glc-Glc, —O-Glc-Gal, —O-Glc-Rha, —O-Gal-Glc, —O-Gal-Gal, —O-Gal-Rha, —O-Glc-Glc-Api, —O-Gal-Glc-Api, —O-Glc-Gal-Api, and —O-Gal-Gal-Api.

2. A flavonol glycoside compound whose compound category is F-7Q. Wherein, the aglycon structure of the compound is Rhamnetin with a molecular weight of 316 or 3,3',4',5-Tetrahydroxy-7-methoxyflavone, or 7-methoxyl-quercetin, and the compound has the following general structure:

(F-7Q)

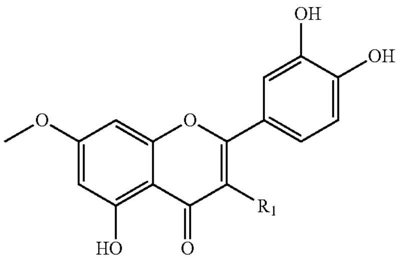

Wherein, $R_1$=glycosyl, which may be selected from the group consisting of —OH, —O-Glc, —O-Gal, —O-Glc-Glc, —O-Glc-Gal, —O-Glc-Api, —O-Glc-Rha, —O-Gal-Glc, —O-Gal-Gal, —O-Gal-Api, —O-Gal-Rha, —O-Glc-Glc-Api, —O-Gal-Glc-Api, —O-Glc-Gal-Api, —O-Gal-Gal-Api, —O-Gal-Rha-Gal, —O-Gal-Rha-Glc, —O-Glc-Rha-Glc, and —O-Glc-Rha-Gal;

3. A flavonol glycoside compound whose compound category is F-74Q. Wherein, the aglycon structure of the compound is Ombuine with a molecular weight of 330 or 3,5,3'-Trihydroxy 7,4'-dimerhoxyflavone, or 7,4'-dimerhoxyl-quercetin, and the compound has the following general structure:

(F-74Q)

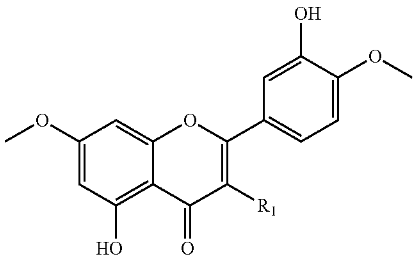

Wherein, $R_1$=glycosyl, which may be selected from the group consisting of —OH, —O-Glc, —O-Gal, —O-Glc-Api, and —O-Gal-Api.

4. A flavonol glycoside compound whose compound category is F-K. Wherein, the aglycone structure of the compound is kaempferol with a molecular weight of 286 or 3,4',5,7-Tetrahydroxyflavone, and the compound has the following general structure:

(F-K)

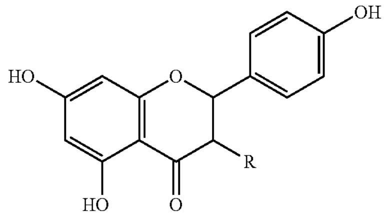

Wherein, R may be selected from the group consisting of —OH, —O-Glc, —O-Gal, —O-Glc-Rha, and —O-Gal-Rha.

5. A flavonol glycoside compound whose compound category is F-Q. Wherein, the aglycone structure is quercetin with a molecular weight of 302 or 3,3',4',5,7-Pentahydroxyflavone, and the compound has the following general structure:

(F-Q)

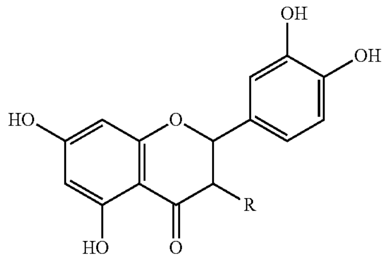

Wherein, R may be selected from the group consisting of —OH, —O-Glc, —O-Gal, —O-Glc-Rha, and —O-Gal-Rha.

6. A flavonol glycoside compound whose compound category is F-74K. Wherein, the aglycone structure is Ermanin with a molecular weight of 314 or 3,5-dihydroxy 7,4'- dimerhoxyflavone, or 7,4'-dimerhoxyl-kaempferol, and the compound has the following general structure:

(F-74K)

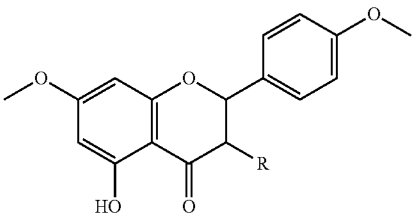

Wherein, R=glycosyl, which may be selected from the group consisting of —OH, —O-Gal, and —O-Gal-Api.

(2) Xanthone Compounds of *Polygala japonica* Houtt.

It can be confirmed by secondary mass spectrometry that the xanthone compounds of *Polygala japonica* Houtt. are selected from the following formulas (II-1), (II-2) and (II-3)

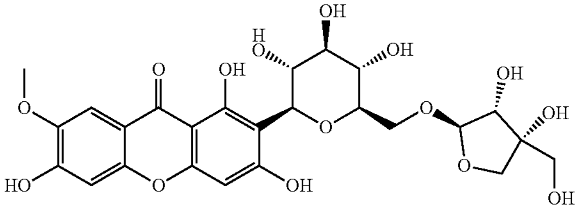 [SMILES: COc1cc2c(=O)c3c(O)c([C@@H]4O[C@H](CO[C@@H]5OC[C@](O)(CO)[C@H]5O)[C@@H](O)[C@H](O)[C@H]4O)c(O)cc3oc2cc1O]

(II-1, polygalaxanthone III)

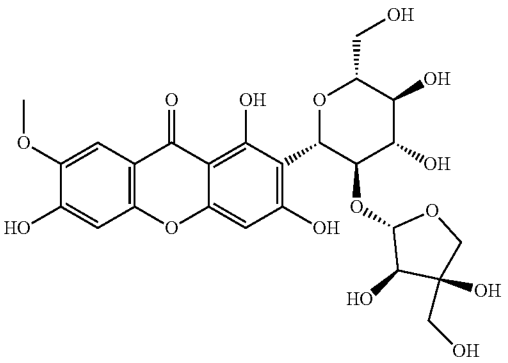 [SMILES: COc1cc2c(=O)c3c(O)c([C@@H]4O[C@H](CO)[C@@H](O)[C@H](O)[C@H]4O[C@@H]4OC[C@](O)(CO)[C@H]4O)c(O)cc3oc2cc1O]

(II-2, polygalaxanthone XI)

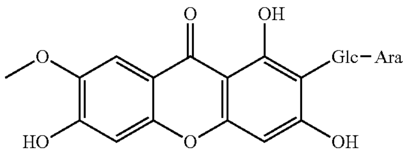

(II-3, polygalaxanthone VIII).

(3) Glycolipid Compounds

It can be confirmed by secondary mass spectrometry that the structure of the glycolipid compound is selected from the following formulas (III-1) and (III-2)

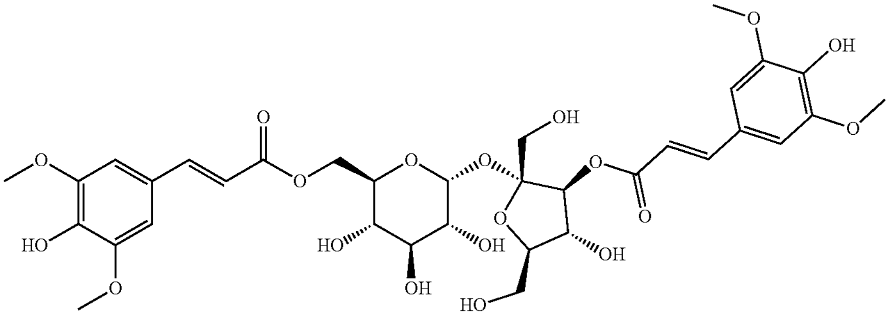

(III-1, 3,6'-disinapoyl sucrose)

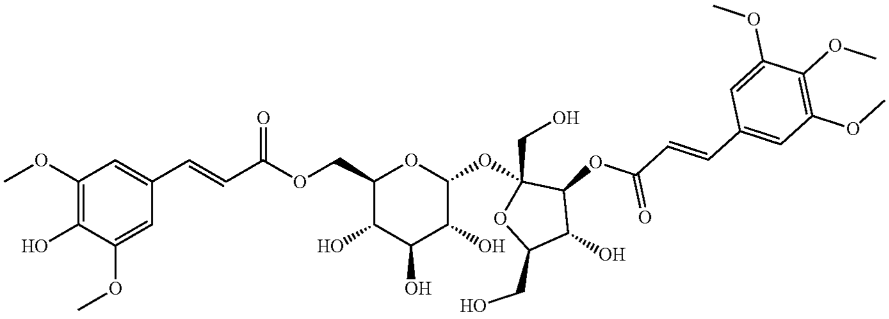

(III-2, Tenuifoliside C).

(4) Saponin Compounds

It can be confirmed by HPLC and multi-stage tandem MS analysis that the alcohol extract from the aboveground part of *Polygala japonica* Houtt. in the present application includes Polygalasaponin VIII, Polygalasaponin XXI, Polygalasaponin X, Polygalasaponin XXIX and other saponin compounds.

The alcohol extract from the aboveground part of *Polygala japonica* Houtt. comprises not only flavonols and xanthones and other target active ingredients, but also saponins, glycolipids and other ingredients. Therefore, the present inventors further tried to further refine the above-mentioned alcohol extract from the aboveground part of *Polygala japonica* Houtt. by separation methods such as macroporous resin and polyamide resin, so as to separate and enrich the target active ingredients.

Preparation Example 5: Macroporous Resin Refining Treatment of Alcohol Extract from the Aboveground Part of *Polygala japonica* Houtt The extract concentrate obtained in Preparation Example 1 was passed through the D101 macroporous adsorption resin column at a flow rate of 1 times the column bed volume per hour. After the adsorption was completed, it was first washed with 8 times the amount of resin to remove impurities, and then washed with 2-5 times the column bed volume of 0%-25, 25%-50%, 50%-75%, 75%-95% ethanol gradient elution, the elution was performed at a flow rate of 0.5-2 times the column bed volume per hour to obtain the eluent; and the ethanol eluate with different concentrations was concentrated 5-20 times respectively to obtain an eluate concentrate with a relative density of 1.1-1.3 g/ml.

The fingerprint analysis was performed for the components of the obtained alcohol extract concentrate of the whole herb of *Polygala japonica* Houtt, and ethanol gradient eluate concentrate through a macroporous adsorption resin column by using HPLC, respectively.

Preparation Example 6: Polyamide Resin Refining Treatment of

Water Extract from the Aboveground Part of *Polygala japonica* Houtt. The extract concentrate obtained in Preparation Example 3 was passed through the polyamide resin column at a flow rate of 0.5-1 times the column bed volume per hour. After the adsorption was completed, it was first washed with 2-8 times the amount of resin to elute and remove impurities, and then washed with 2-5 times column bed volume of 0-25%, 25%-50%, 50%-75%, 75%-95% ethanol gradient elution, the elution was performed at a flow rate of 0.5-2 times column bed volume per hour to obtain the eluent; the above-mentioned ethanol eluate with different concentrations was concentrated 5-20 times respectively to obtain an eluate concentrate with a relative density of 1.1-1.3 g/ml.

Comparing the separation effect of macroporous resin and polyamide resin, it can be found that polyamide resin can better remove the saponin component of the extract of *Polygala japonica* Houtt., and the separation and purification effect is better.

The fingerprint analysis was performed for the components of the obtained extract concentrate of the aboveground part of *Polygala japonica* Houtt, and ethanol gradient eluate concentrate through a polyamide resin column by using HPLC, respectively.

Figure 3:
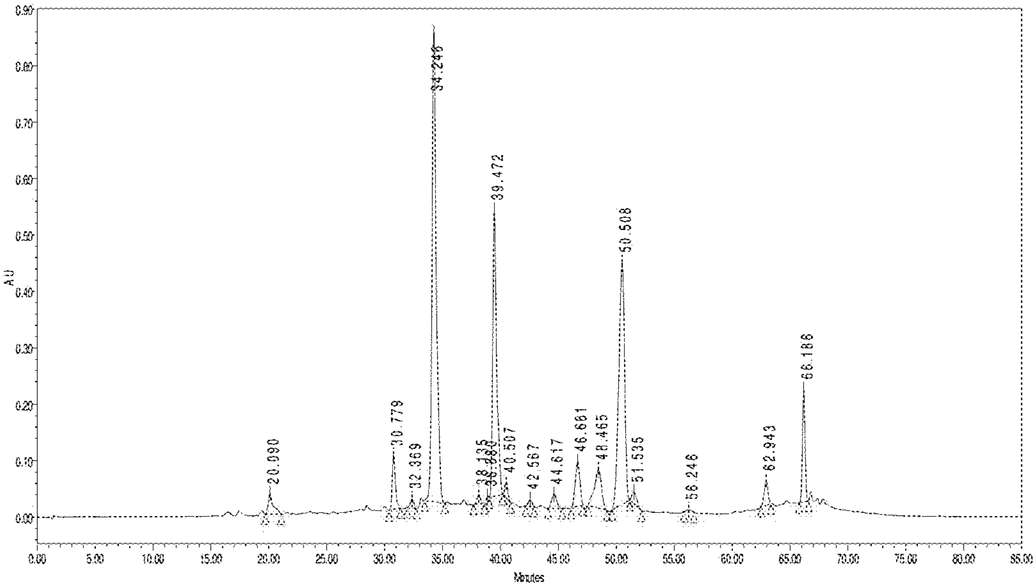
FIG. 3 is the HPLC analysis chromatogram of the effective part obtained after the polyamide resin gradient elution of the aboveground part of *Polygala japonica* Houtt. of the present invention.
Figure 4:
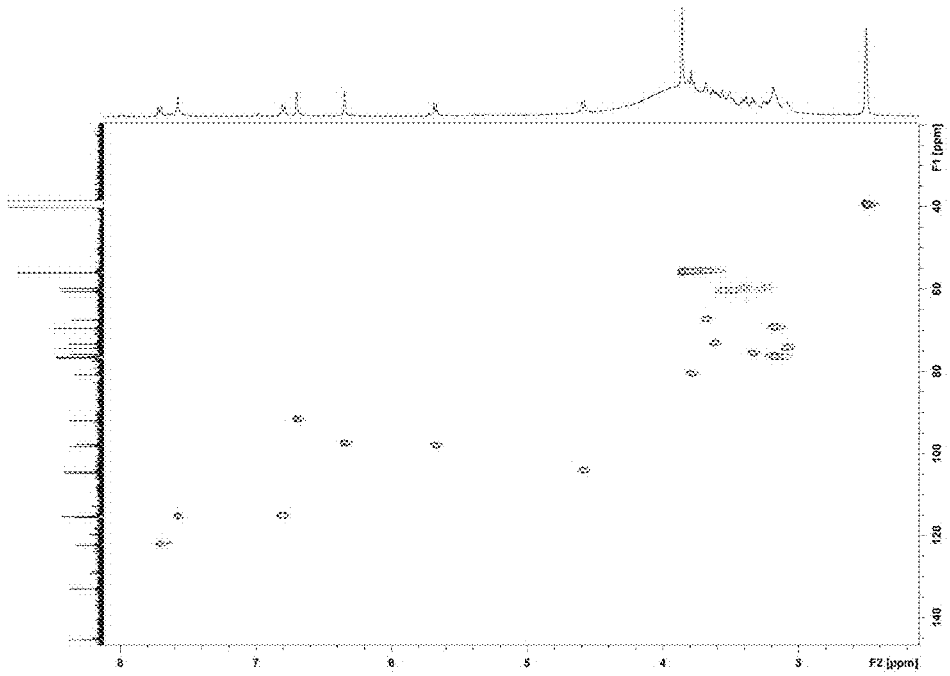
FIG. 4 is the C—H correlation two-dimensional NMR chromatogram of the compound F-7Q-1 of the present invention.
Figure 5:
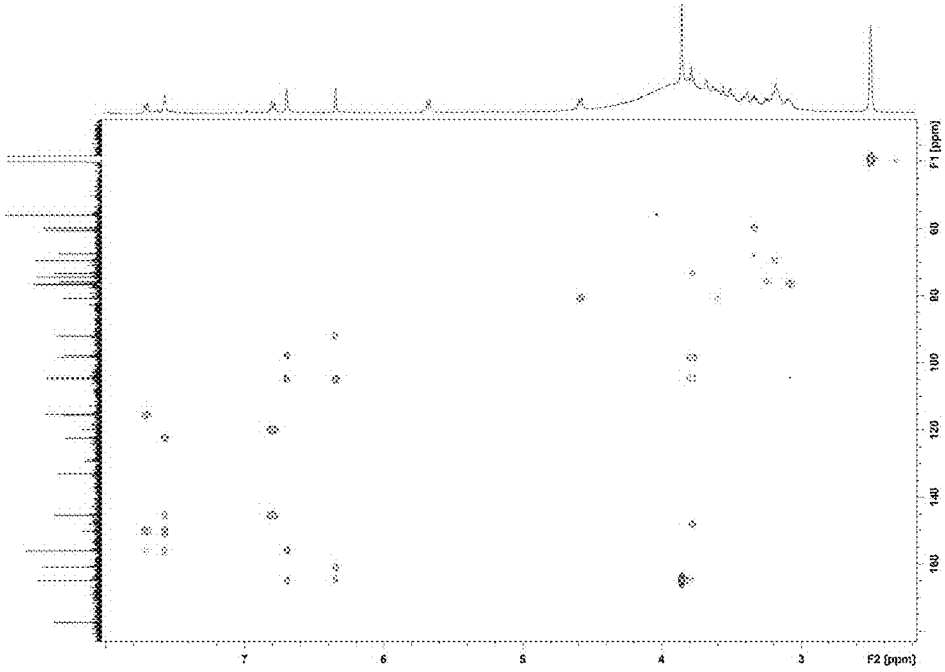
FIG. 5 is the C—H remote two-dimensional NMR correlation chromatogram of the compound F-7Q-1 of the present invention.
Figure 6:
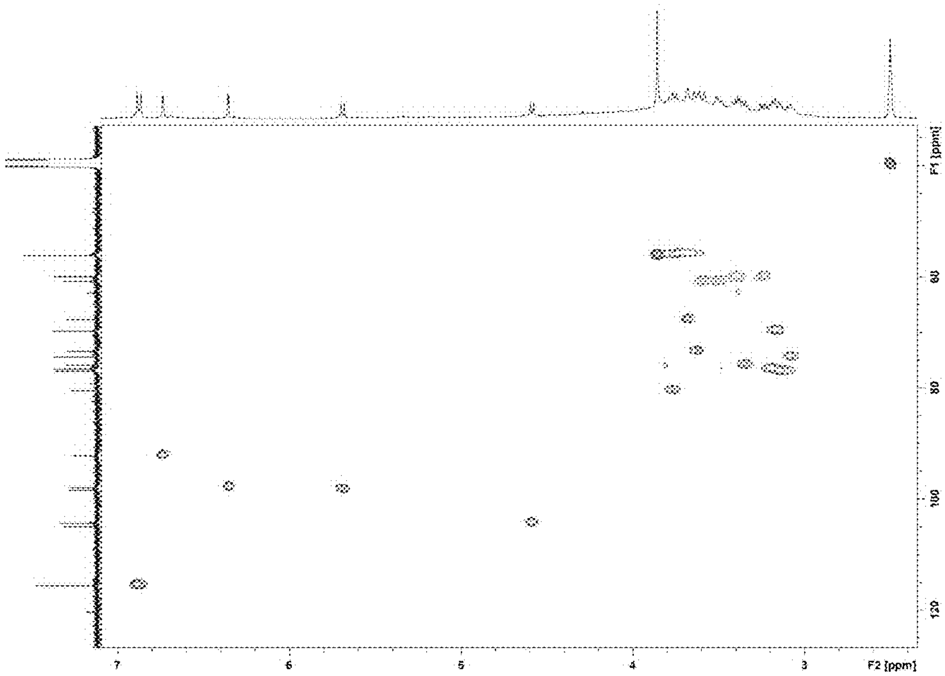
FIG. 6 is the C—H correlation two-dimensional NMR chromatogram of the compound F-7K-1 of the present invention.
Figure 7:
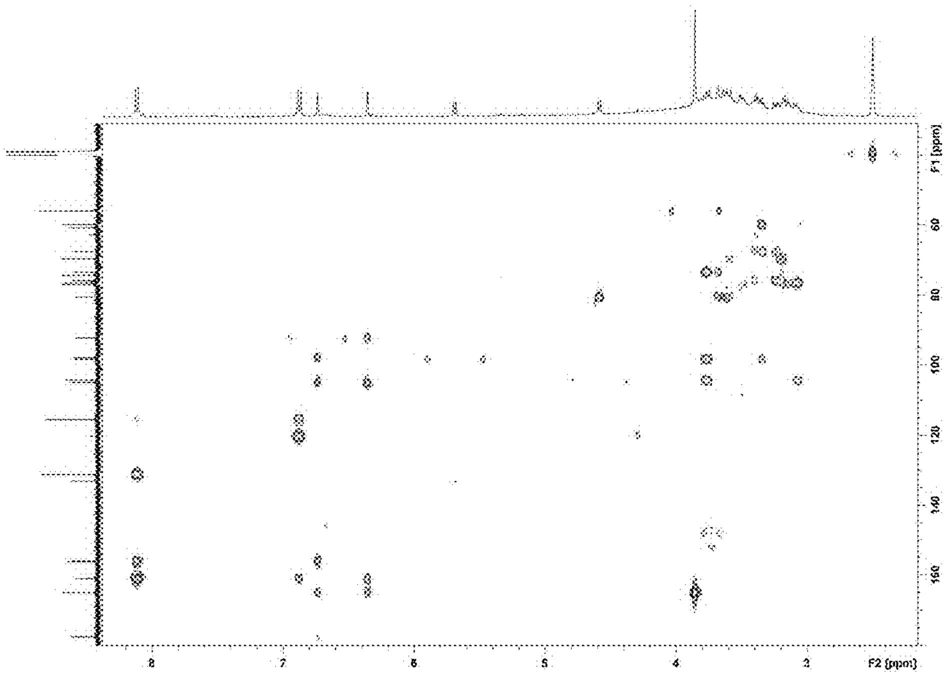
FIG. 7 is the C—H remote correlation two-dimensional NMR chromatogram of the compound F-7K-1 of the present invention.
Figure 8:
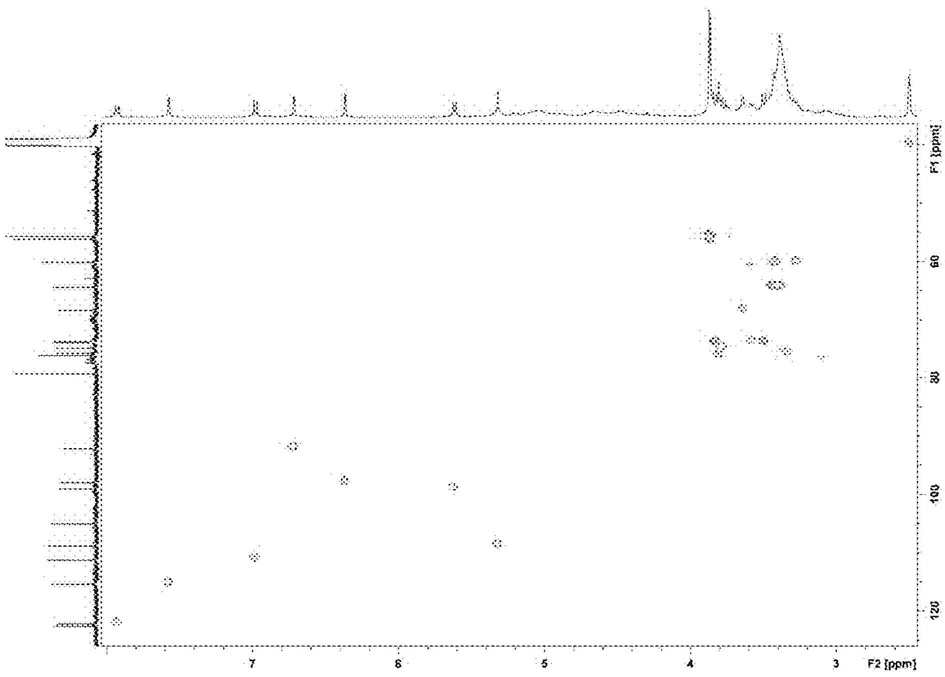
FIG. 8 is the C—H correlation two-dimensional NMR chromatogram of the compound F-74Q-1 of the present invention
Figure 9:
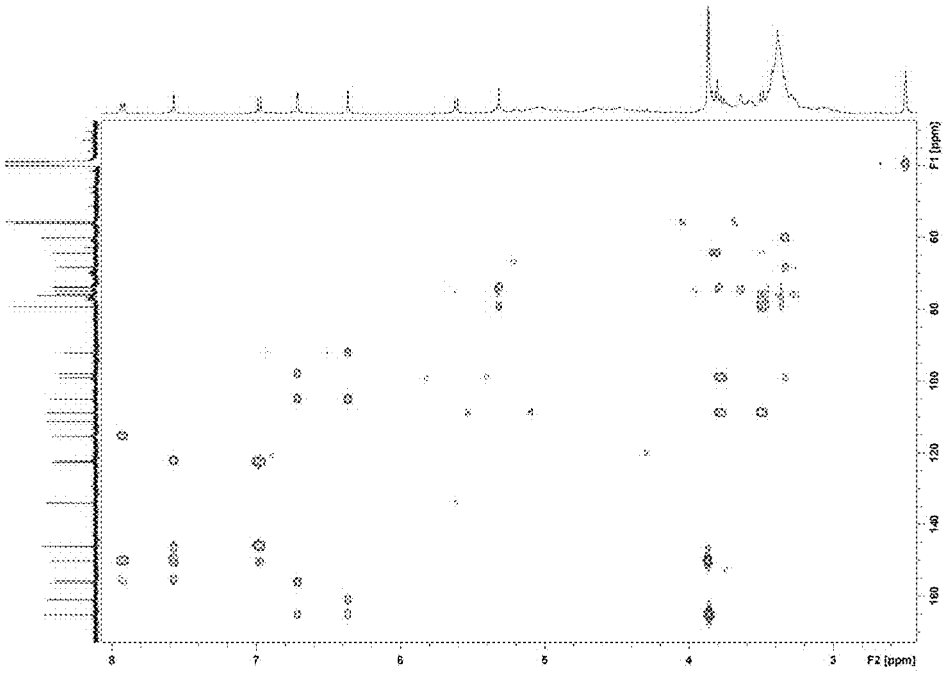
FIG. 9 is the C—H remote correlation two-dimensional NMR chromatogram of the compound F-74Q-1 of the present invention
Figure 10:
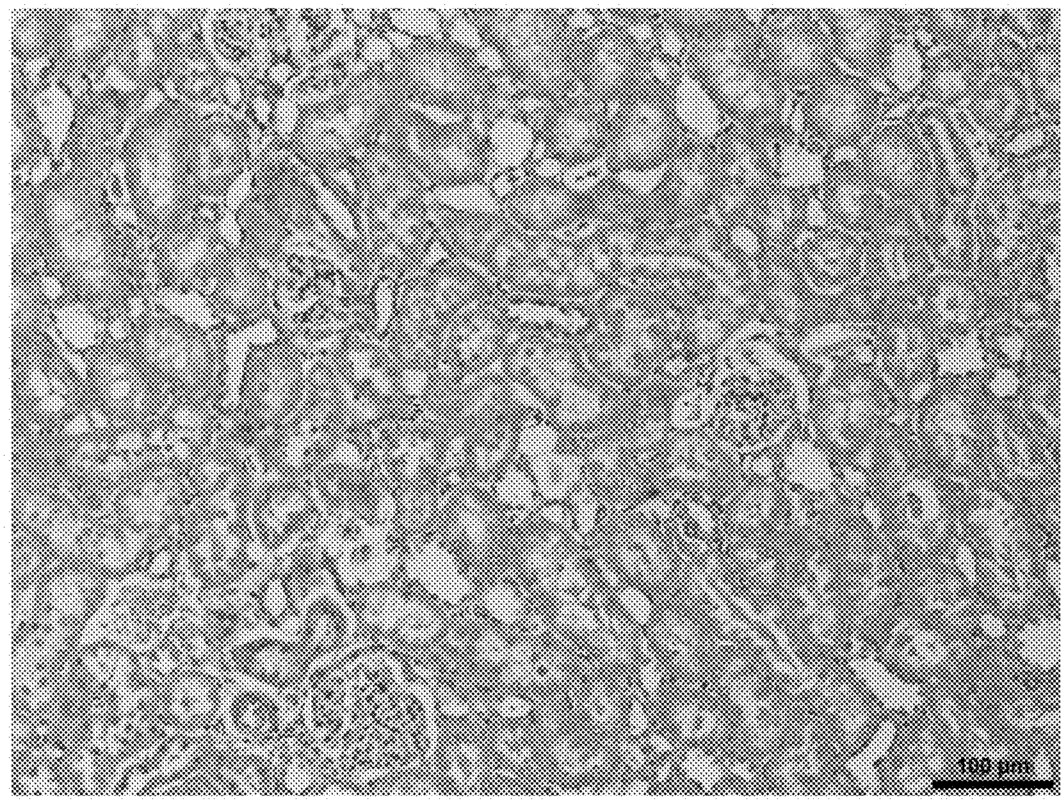
FIG. 10 is the observation result under HE microscope of the renal tubule dilatation lesion animal test using the drug of the present invention (normal group).
Figure 11:
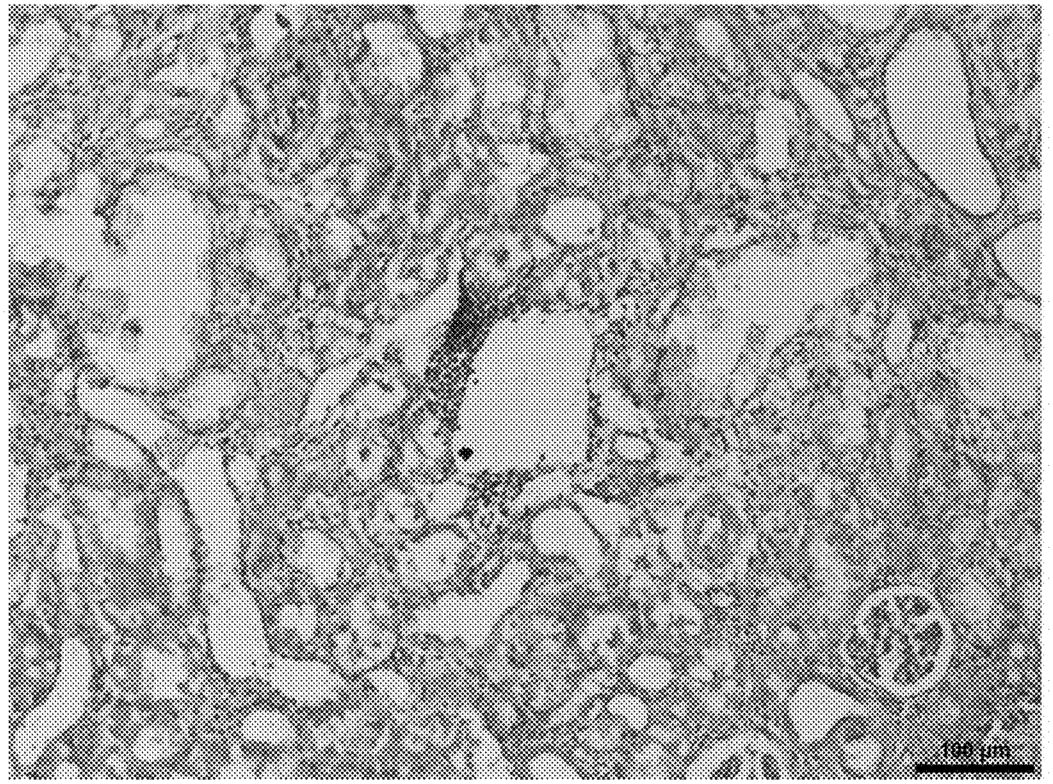
FIG. 11 is the observation result under HE microscope of the renal tubule dilatation lesion animal test using the drug of the present invention (model group).
Figure 12:
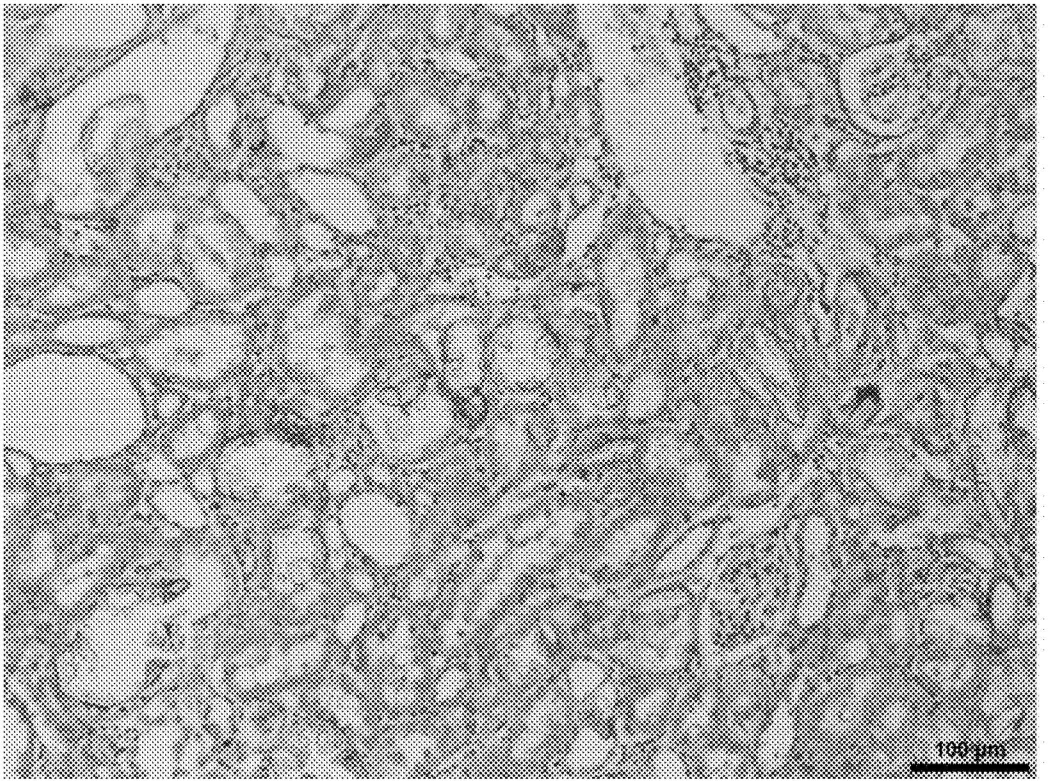
FIG. 12 is the observation result under HE microscope of the renal tubule dilatation lesion animal test using the drug of the present invention (potassium sodium hydrogen citrate drug group).
Figure 13:
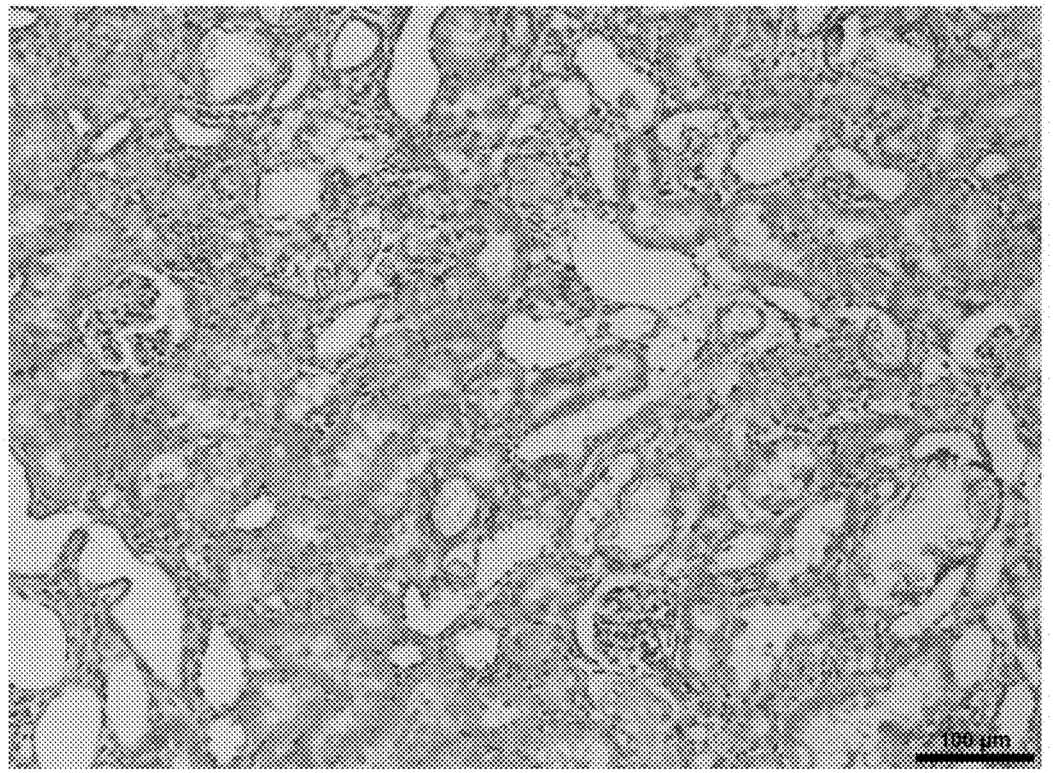
FIG. 13 is the observation result under HE microscope of the renal tubule dilatation lesion animal test using the drug of the present invention (low dose group).
Figure 14:
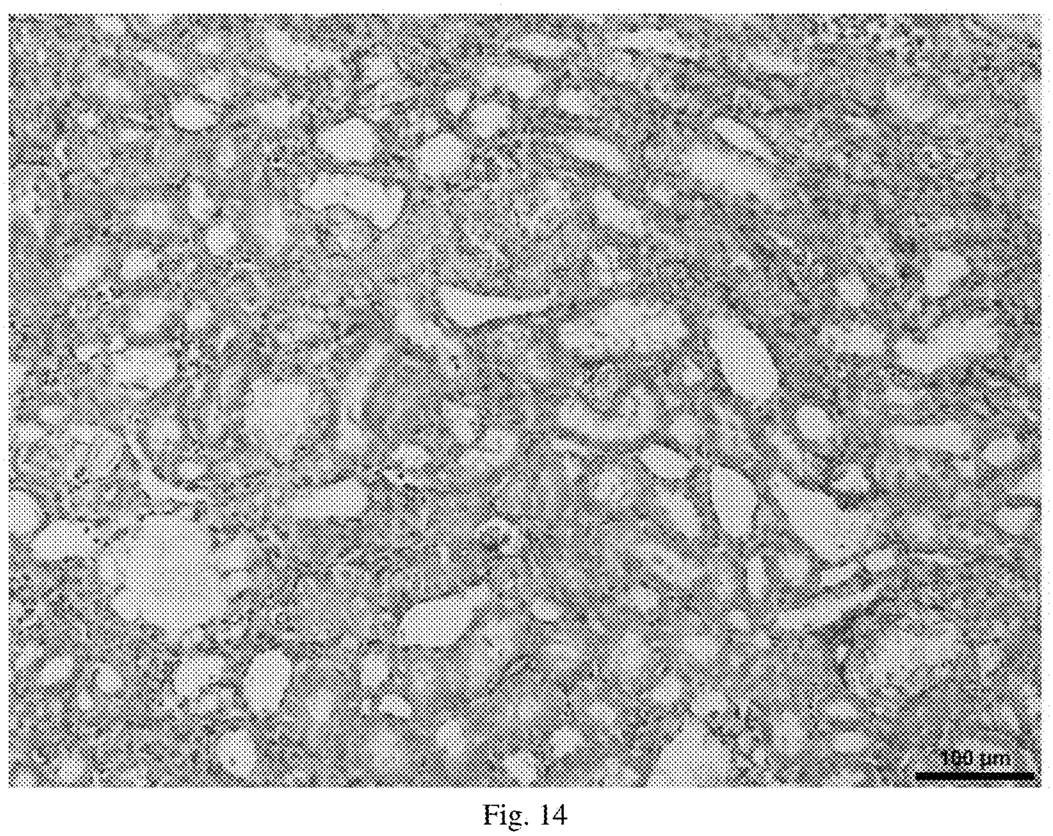
FIG. 14 is the observation result under HE microscope of the renal tubule dilatation lesion animal test using the drug of the present invention (middle dose group).
Figure 15:
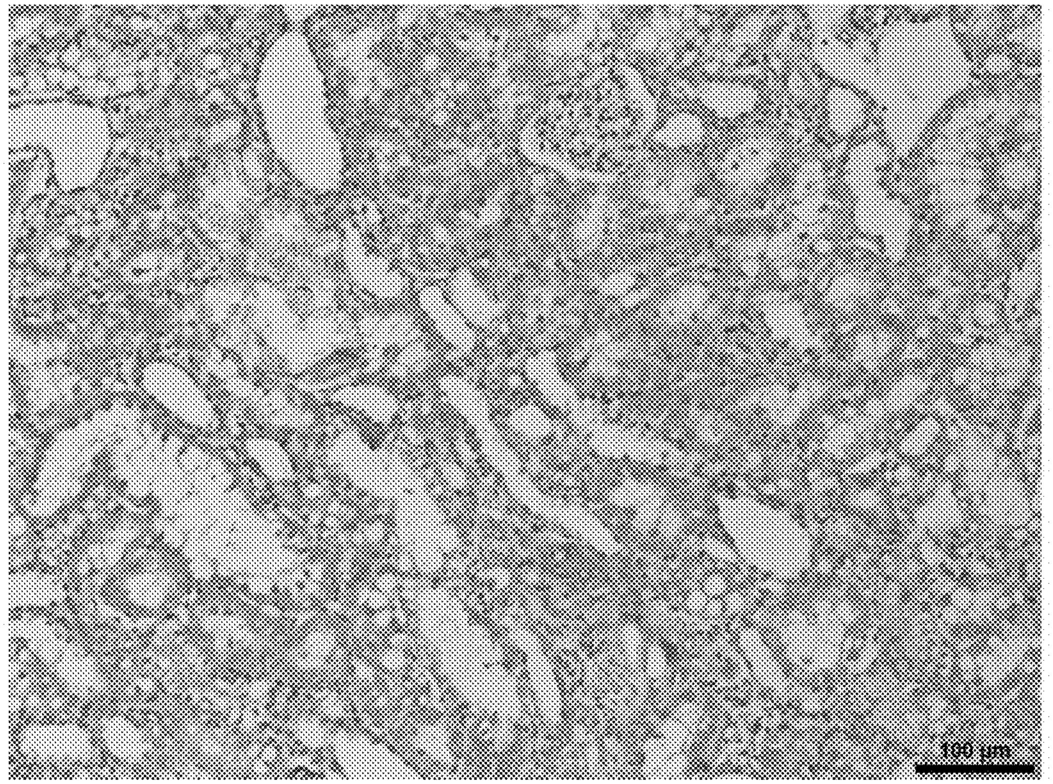
FIG. 15 is the observation result under HE microscope of the renal tubule dilatation lesion animal test using the drug of the present invention (high dose group).

It is confirmed by HPLC analysis that the total content of active ingredients (I), (II) and (III) is 50%-90% in the orange-red eluate concentrate of the 0-25% ethanol elution part (as shown in FIG. 3 of the specification).

The eluate concentrate was dried under reduced pressure at 75° C. and crushed to obtain the enriched active ingredients of the aboveground part of *Polygala japonica* Houtt., which were used in the drug efficacy comparison experiment.

The enriched active ingredients of the aboveground part of *Polygala japonica* Houtt. were analyzed by HPLC-MS, and the MS analysis included positive and negative ions, MS-MS, MS-MS-MS analysis, and the analysis results were compared with the existing literature to confirm the compound structure shown in Table 2 below.

TABLE 2

Components analysis of water extraction-polyamide resin refined extract of aboveground part of *Polygala japonica Houtt.*

| No. | Retention time(LC) | Compound category | Molecular weight | Molecular formula and sugar chain | Structure confirmation | Area % |
|---|---|---|---|---|---|---|
| 1 | 20.090 | Xanthones | 568 | $C_{25}H_{28}O_{15}$ | Polygalaxanthone III | 1.74 |
| 2 | 30.779 | Glycolipids | 754 | $C_{34}H_{42}O_{19}$ | 3,6'-disinapoyl sucrose | 2.86 |
| 3 | 32.369 | F-7Q | 640 | $C_{28}H_{32}O_{17}$ 316-162-162 | Rhamnetin + Glc (or Gal) + Glc (or Gal) Isomers with F-7Q-1 | 0.52 |
| 4 | 34.243 | F-7Q-1 | 640 | $C_{28}H_{32}O_{17}$ 316-162-162 | Rhamnetin 3-O-β-D-Glucopyranosyl (1→2)-β-D-galactopyranoside | 33.71 |
| 5 | 38.100 | F-7K | 756 | $C_{33}H_{40}O_{20}$ 300-162-132-162 | Rhamnocitrin + Glc (or Gal) + Api + Glc (or Gal) Isomers with Peak No. 6 | 0.50 |
| 6 | 38.802 | F-7K | 756 | $C_{33}H_{40}O_{20}$ 300-162-132-162 | Rhamnocitrin + Glc (or Gal) + Api + Glc (or Gal) Isomers with Peak No. 5 | 0.12 |
| 7 | 39.472 | F-7K-1 | 624 | $C_{28}H_{32}O_{16}$ | Rhamnocitrin 3-O-β-D-glucopyranosyl (1→2)-β-D-galactopyranoside | 18.97 |
| 8 | 40.507 | F-7Q | 610 | $C_{27}H_{30}O_{16}$ 316-162-132 | Polygalin E or Polygalin F | 0.76 |
| 9 | 42.567 | F-7Q | 478 | $C_{22}H_{22}O_{12}$ 316-162 | Rhamnetin + Glc (or Gal) | 0.42 |

TABLE 2-continued

Components analysis of water extraction-polyamide resin refined extract of aboveground part of *Polygala japonica Houtt.*

| No. | Retention time(LC) | Compound category | Molecular weight | Molecular formula and sugar chain | Structure confirmation | Area % |
|---|---|---|---|---|---|---|
| 10 | 44.617 | Glycolipids | 768 | C35H44O19 | Tenuifoliside C | 1.19 |
| 11 | 46.661 | F-7K | 594 | C27H30O15 300-162-132 | Rhamnocitrin + Glc (or Gal) + Api | 3.48 |
| 12 | 47.667 | F-7K | 462 | C22H22O11 300-162 | Rhamnocitrin + Glc (or Gal) | 4.62 |
| 13 | 50.508 | F-74Q-1 | 624 | C28H32O16 330-162-132 | Polygalin C, 3,5,3'-trihydroxy-7,4'-dimethoxyflavone-3-O-β-D-apiofranosyl (1→2)-β-D-galactopyranoside | 23.60 |
| 14 | 51.535 | F-74Q | 624 | C28H32O16 330-162-132 | Polygalin D Isomers with Polygalin C | 0.79 |
| 15 | 56.047 | F-74Q | 492 | C23H24O12 330-162 | 3,5,3'-Trihydroxy 7,4'-dimerhoxyflavone + Glc (or Gal) | 0.20 |
| 16 | 62.943 | F-7K | 770 | C34H42O20 300-162-162-146 | Rhamnocitrin + 2Glc (or Gal) + Rha | 1.53 |
| 17 | 66.186 | F-74K-1 | 608 | C28H32O15 314-(162 + 132) | Polygalin B, 3,5-Dihydroxy-7,4'-dimethoxyflavone-3-O-β-D-apiofranosyl (1→2)-β-D-galactopyranoside | 4.81 |

Based on the above analysis, it can be confirmed that the main components of the water extraction-polyamide refined extract of *Polygala japonica* Houtt. comprises flavonol compounds with compound categories of F-7K, F-7Q, F-74Q, F-74K, and the xanthone compound of formula (II-1) (polygalaxanthone III) and glycolipid compounds.

In Table 2, the compound with a content of 18.97% is identified as F-7K-1, the compound with a content of 33.71% is identified as F-7Q-1, the compound with a content of 23.60% is identified as F-74Q-1, and the compound with a content of 4.81% is identified as compound F-74K-1 (Polygalitol B).

Wherein the meanings of the above compound category names are exactly the same as those in Table 1.

It needs to be emphasized that due to the difference in the extracted specific parts (whole herb, rhizome, or stem and leaf) of the plant *Polygala japonica* Houtt., the difference in the source of origin, and the difference in the preparation of the plant *Polygala japonica* Houtt. (commercially available dried herbs, fresh plant *Polygala japonica* Houtt.) as well as the difference in the specific extraction and refining process conditions may lead to different degrees of differences in the structure and content of the active ingredient in the obtained active ingredient extract. In the present invention, preferably the active ingredient extract was obtained from fresh or dried aboveground parts of *Polygala japonica* Houtt. by water extraction and polyamide column alcohol/water gradient elution.

Preparation Example 7: Separation and Refining of Main Active Compounds

It can be determined by HPLC-MS-MS whether it is a single sugar chain according to the obvious characteristics when determining the parent core of the flavonol compound and the presence of multiple sugar rings in the molecule. However, there is insufficient basis for discriminating the configuration of the hydroxyl group on a certain carbon atom of a sugar ring with the same molecular weight (such as glucose or galactose). When a sugar chain has more than two sugar rings, there is insufficient basis for determining the linkage position of the sugar (for example, a 1-2 linkage, a 1-4 linkage, or a 1-6 linkage) and a or β configuration of the sugar configuration. To this end, the pure compound of the main active ingredient was separated by semi-preparative HPLC, and its specific structure was determined in combination with H NMR, C NMR, and two-dimensional NMR.

Purification was performed by semi-preparative HPLC. The extract prepared in Example 5 was further separated and purified, and the pure single compounds of the three components with the highest content in the extract were collected respectively, that is, the pure single compounds of compounds F-7Q-1, F-7K-1, and F-74Q-1 were obtained.

The semi-preparative HPLC instrument and conditions were as follows:

HPLC test conditions mobile phase: acetonitrile (A), deionized water (B), binary gradient separation;

Semi-preparative column: 19×250 mm, C18

Flow rate: 8 mL·min-1;

Detection wavelength: 330 nm;

Column temperature: room temperature;

Injection volume: 0.5 mL.

Chromatogram was recorded for 180 min.

The structures of compounds F-7Q-1, F-7K-1, and F-74Q-1 were analyzed by NMR and two-dimensional NMR, respectively. The analysis results were as follows:

1. Confirmation of the Structure of Compound F-7Q-1

Molecular weight: 640, sugar chain: 316-162-162,

The key information related to the two-dimensional NMR of compound F-70-1 was summarized in the following table:

| No. | δH | δC | H—H COSY | HMBC (H→C) |
|---|---|---|---|---|
| 2 | — | 156.1 | | |
| 3 | — | 133.0 | | |
| 4 | — | 177.4 | | |
| 5 | — | 160.9 | | |

-continued

| No. | δH | δC | H—H COSY | HMBC (H→C) |
|---|---|---|---|---|
| 6 | 6.34 (1H, s) | 97.8 | | C-5, 7, 8, 10 |
| 7 | — | 164.9 | | |
| 8 | 6.69 (1H, s) | 92.0 | | C-6, 7, 9, 10 |
| 9 | — | 156.1 | | |
| 10 | — | 104.8 | | |
| 1' | — | 119.9 | | |
| 2' | 7.57 (1H, s) | 115.5 | | C-2, 1', 3', 4' |
| 3' | — | 145.4 | | |
| 4' | — | 150.3 | | |
| 5' | 6.81 (1H, d, J = 8.4) | 115.3 | H-6' | C-1', 3' |
| 6' | 7.72 (1H, d, J = 8.4) | 122.4 | H-5' | C-2, 2', 4' |
| —OCH3 | 3.86 (3H, s) | 56.1 | | |
| Gal-1" | 5.69 (1H, d, J = 7.6) | 98.4 | | C-3, 3" |
| 2" | 3.79 (m) | 80.9 | | |
| 3" | 3.59 (m) | 73.4 | | |
| 4" | 3.64 (m) | 67.6 | | |
| 5" | 3.35 (m) | 75.9 | | |
| 6" | 3.26, 3.42 (m) | 59.9 | | |
| Glu-1''' | 4.60 (1H, d, J = 7.7) | 104.4 | | C-2" |
| 2''' | 3.09 (m) | 74.5 | | |
| 3''' | 3.18 (m) | 76.8 | | |
| 4''' | 3.21 (m) | 69.5 | | |
| 5''' | 3.23 (m) | 76.6 | | |
| 6''' | 3.51, 3.56 (m) | 60.6 | | |

Based on the above chromatographic analysis data, it is finally confirmed that the exact spatial structural formula of the main active ingredient compound F-7Q-1 is as follows:

(F-7Q-1)

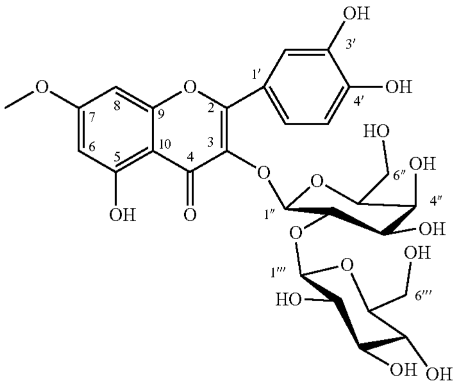

The compound name of F-7Q-1 is: Rhamnetin 3-O-β-D-glucopyranosyl (1→2)-β-D-galactopyranoside, or Rhamnetin-3-O-(2"-O-β-D-glucopyranosyl)-β-D-galactopyranoside.

(2) Confirmation of the Structure of Compound F-7K-1

Molecular weight: 624, sugar chain: 300-162-162,

The key information related to the two-dimensional NMR of compound F-7K-1 was summarized in the following table:

| No. | δH | δC | H—H COSY | HMBC (H→C) |
|---|---|---|---|---|
| 2 | — | 156.2 | | |
| 3 | — | 133.0 | | |
| 4 | — | 177.6 | | |
| 5 | — | 161.0 | | |
| 6 | 6.36 (1H, d, J = 2.2) | 97.9 | | C-5, 7, 8, 10 |
| 7 | — | 165.0 | | |
| 8 | 6.74 (1H, d, J = 2.2) | 92.2 | | C-6, 7, 9, 10 |
| 9 | — | 156.0 | | |
| 10 | — | 104.9 | | |

-continued

| No. | δH | δC | H—H COSY | HMBC (H→C) |
|---|---|---|---|---|
| 1' | — | 120.2 | | |
| 2', 6' | 8.13 (2H, d, J = 8.9) | 131.1 | H-3', 5' | C-2, 2', 4', 6' |
| 3', 5' | 6.89 (2H, d, J = 8.9) | 115.5 | H-2', 6' | C-1', 3', 4', 5' |
| 4' | — | 161.0 | | |
| —OCH3 | 3.86 (3H, s) | 56.1 | | C-7 |
| Gal-1" | 5.70 (1H, d, J = 7.6) | 98.3 | | C-3, 3" |
| 2" | 3.78 (m) | 80.5 | | |
| 3" | 3.58 (m) | 73.4 | | |
| 4" | 3.64 (m) | 67.6 | | |
| 5" | 3.34 (m) | 75.9 | | |
| 6" | 3.27, 3.43 (m) | 59.9 | | |
| Glu-1''' | 4.60 (1H, d, J = 7.8) | 104.3 | | C-2" |
| 2''' | 3.08 (m) | 74.4 | | |
| 3''' | 3.18 (m) | 77.0 | | |
| 4''' | 3.21 (m) | 69.7 | | |
| 5''' | 3.34 (m) | 76.6 | | |
| 6''' | 3.51, 3.56 (m) | 60.8 | | |

Based on the above chromatographic analysis data, it is finally confirmed that the exact spatial structural formula of the main active ingredient compound F-7K-1 is as follows:

(F-7K-1)

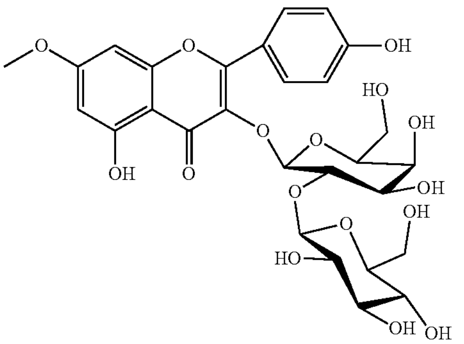

The compound name of F-7K-1 is: Rhamnocitrin 3-O-β-D-glucopyranosyl (1→2)-β-D-galactopyranoside or OR Rhamnocitrin-3-O-(2"-O-β-D-glucopyranosyl)-β-D-galactopyranoside.

3. Confirmation of the Structure of Compound F-74Q-1

Molecular weight: 624, sugar chain: 330-162-132, identification:

The key information related to the two-dimensional NMR of compound F-74Q-1 was summarized in the following table:

| No. | δH | δC | H—H COSY | HMBC (H→C) |
|---|---|---|---|---|
| 2 | — | 155.7 | | |
| 3 | — | 133.8 | | |
| 4 | — | 177.6 | | |
| 5 | — | 161 | | |
| 6 | 6.36 (1H, d, J = 2.1) | 97.9 | | C-5, 7, 8, 10 |
| 7 | — | 165.0 | | |
| 8 | 6.74 (1H, d, J = 2.1) | 92.1 | | C-6, 7, 9, 10 |
| 9 | — | 156.2 | | |
| 10 | — | 105 | | |
| 1' | — | 122.6 | | |
| 2' | 7.57 (1H, d, J = 2.2) | 115.3 | | C-2, 1', 3' ,4' |
| 3' | — | 146.1 | | |
| 4' | — | 150.2 | | |
| 5' | 6.98 (1H, d, J = 8.8) | 111.2 | H-5', 6' | C-1', 3', 4' |
| 6' | 7.93 (1H, dd, J = 8.8, 2.2) | 122.2 | H-5', 6' | C-2, 2', 4' |
| 7-OCH3 | 3.87 (3H, s) | 56.1 | | C-7 |

-continued

| No. | δH | δC | H—H COSY | HMBC (H→C) |
|---|---|---|---|---|
| 4'-OCH3 | 3.86 (3H, s) | 55.7 | | C-4 |
| Gal-1" | 5.62 (1H, d, J = 8.0) | 99.0 | | C-3, 3" |
| 2" | 3.78(m) | 74.9 | | |
| 3" | 3.58(m) | 73.8 | | |
| 4" | 3.64(m) | 68.3 | | |
| 5" | 3.34(m) | 75.8 | | |
| 6" | 3.43, 3.28(m) | 60.1 | | |
| Api-1''' | 5.32 (1H, d, J = 1.0) | 108.8 | | C-2", 2''', 3''' |
| 2''' | 3.80(m) | 76.1 | | |
| 3''' | — | 79.1 | | |
| 4''' | 3.51(m), 3.84(m) | 73.9 | | |
| 5''' | 3.46(m), 3.39(m) | 64.3 | | |

Based on the above chromatographic analysis data, it is finally confirmed that the exact spatial structural formula of the main active ingredient compound F-74Q-1 is as follows:

(F-74Q-1)

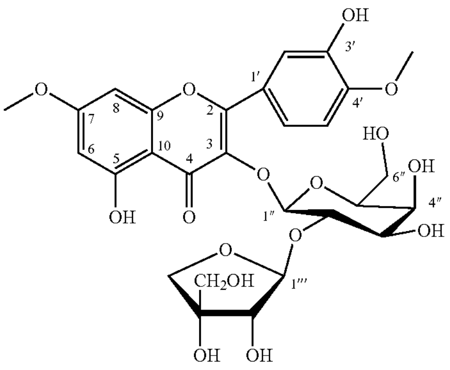

The compound name of F-74Q-1 is: 3,5,3'-trihydroxy-7, 4'-dimethoxyflavone-3-O-β-D-apiofranosyl (1→2)-β-D-galactopyranoside, or Polygalin C, or Polygalitol C.

Based on the inventors' research, the inventors believe that the isolated compounds F-7Q-1, F-7K-1, and F-74Q-1, as the main component of the *Polygala japonica* Houtt. extract of the present invention, play a key role for realizing the desired pharmaceutical effect. These compounds have a hydroxyl group as a substituent at the β position of the carbonyl in the described molecular structure, the hydroxyl group and the ketone carbonyl group act together to more effectively react with calcium ion-containing components of the calculus in the urinary system, thereby more effectively degrading or dissolving the calculus in the urinary system. Therefore, at least one of the compounds F-7Q-1, F-7K-1, and F-74Q-1 can also be used as the main and necessary active ingredient to prepare a corresponding pharmaceutical composition for treating or preventing urolithiasis and urinary tract infections or kidney damage caused by urolithiasis, and as an adjuvant drug after surgical treatment of urolithiasis. The pharmaceutical composition may further comprises pharmaceutically acceptable adjuvants, carriers or excipients.

II. Experimental Example of Pharmacological Activity

1. Preparation of Test Samples

① High-dose group test sample: the water-extracted, 0-25% ethanol gradient eluent by polyamide column prepared in Preparation Example 5 was concentrated and dried to obtain the active ingredient extract. A solution with a density of about 1.2 g/ml was formulated, and the concentration of the effective substance measured by the pharmacopoeia standard and the absorbance method (using rutin as a standard substance to make a standard curve) is about 130.4 mg/ml.

② Medium-dose group test sample: the high-dose group sample was diluted once to obtain the middle-dose group test sample.

③ Low-dose group test sample: the middle-dose group sample was dilute once to obtain the low-dose group test sample.

④ Positive control group test sample: potassium sodium hydrogen citrate aqueous solution with a concentration of 100 mg/ml, 3 ml per day, equivalent to 300 mg/d.

2. Animal Experiments 2.1. Experimental Animals and Feeding Conditions

36 SD rats were purchased from Shanghai Slack, license number: SCXK (Shanghai) 2017-0005, certificate number: 20170005011248. Drinking water is ultrapure water. The license number for the experimental animal room is SYXK (Zhejiang) 2015-0008.

Feeding environment: temperature ranges from 20° C. to 25° C., and relative humidity ranges from 40% to 70%. Adaptive feeding was performed for one week before the experiment.

2.2. Experimental Scheme 2.2.1 Experimental Animals 36 male SD rats of SPF grade, 6-8 weeks old, 200-250 g.

2.2.3 Model Preparation

SD rats were fed adaptively for 7 days, and all groups (except the normal group) were administered 1% ethylene glycol (by drinking water)+2% ammonium chloride (by intragastric administration) 2 ml/rat to establish a model for 28 consecutive days.

2.2.4 Experimental Grouping and Processing 36 male SD rats were randomly divided into 6 groups according to body weight, 6 rats in each group. These are normal group, model group, potassium sodium hydrogen citrate group, traditional Chinese medicine extract (low, medium, high) dose group. During the modeling process, 3 ml of the drug was administered by intragastric administration every day, and the drug included the positive control drug and the purified part through the polyamide column. The animals were euthanized after 4 weeks.

2.2.5 Kidney

The kidney tissues were peeled off in vivo, the kidney on one side was stored in a cryopreservation tube at −80° C. for tissue homogenate to detect Ca2+ concentration, and the kit operation steps were the same as above; the kidney on the other side was fixed in formalin solution for tissue sectioning to perform HE staining.

(1) The steps for making paraffin sections were as follows:

① fixation, ② trimming, ③ dehydration, ④ transparency, ⑤ wax immersion, ⑥ embedding, ⑦ slicing, ⑧ baking slices, ⑨ preservation: packed in boxes and stored at room temperature.

(2) HE staining steps were as follows:

① dewaxing and rehydration, ② dyeing, ③ dehydration, transparency, mounting,

④ staining results: the nucleus was blue, the cytoplasm was pink, and the red blood cells were bright red.

3. Test Results 3.1. Positive Test Results for Calcium Oxalate Crystals in Rat Urine The results of the urine routine report showed that except the normal group, the calcium oxalate crystals in the urine of the rats in the other groups were all positive.

3.2. Serum Ca2+ Concentration Test Results

The difference in Ca2+ concentration in serum was small among groups. Compared with the normal group, the model group and the middle-dose treatment group had significant differences. The Ca2+ concentration in urine had a large difference. Compared with the normal group, the low-dose treatment group and the high-dose treatment group had very significant differences ($P<0.01$). Compared with the model group, the low-dose treatment group had a very significant difference ($P<0.01$). Potassium sodium hydrogen citrate drug group had the highest concentration in kidney tissue, and there was a very significant difference ($P<0.01$) compared with the model group and the normal group; the other groups had no significant difference.

The CRE levels in serum from high to low were model group>medium dose treatment group>potassium sodium hydrogen citrate drug group>low dose treatment group>high dose treatment group>normal group. Compared with the normal group, the middle-dose treatment group and the high-dose treatment group showed significant differences ($P<0.05$), and there was no significant difference in the other groups.

The BUN levels in serum from high to low were model group>low dose treatment group>potassium sodium hydrogen citrate drug group>medium dose treatment group>high dose treatment group>normal group. Compared with normal group, each groups all had very significant differences ($P<0.01$);

Compared with the model group, except that the low-dose treatment group had a significant difference ($P<0.05$), all other groups had very significant differences ($P<0.01$).

3.3. Observation Results of Lesions Under HE Microscope

The results consisted of three parts: calcium oxalate crystal aggregation, renal tubule dilation lesions, and chronic renal interstitial inflammatory cell infiltration.

The characteristics of the animal model were as follows:

After four weeks, the BUN content in serum of the model animals increased significantly. There was no significant change in blood P, CA content, but the 24-hour urinary OX and CA excretion and renal tissue CA content all increased significantly. It can be observed by naked eyes that the kidneys were enlarged, and the cross-section was pale. The renal cross-section had an obvious friction feeling of fine sand when touched by hand, and the boundary between the renal cortex and renal medulla was unclear. Compared with the normal group, the model group clearly showed: calcium oxalate crystal aggregation, renal tubular epithelial cell swelling, degeneration, necrosis, dilation of the lumen, and chronic renal interstitial inflammatory cell infiltration.

As shown in FIGS. 10 to 15 of the specification, it can be seen under the HE microscope that compared with the normal group, the renal tubules in the model group were significantly dilated, and a large number of brownish yellow calcium oxalate crystals were seen, and inflammatory cells infiltrated in the local renal interstitium; compared with the model group, in the middle and high dose groups, the renal tubule dilatation was improved, the brownish yellow calcium oxalate crystals were significantly reduced, and there was no obvious inflammatory cell infiltration in the renal interstitium; in the low dose group, the renal tubule dilatation was improved, there was no obvious inflammatory cell infiltration in the renal interstitium, the brownish yellow calcium oxalate crystals did not decrease significantly; in the potassium sodium hydrogen citrate group, the renal tubule dilatation was improved, and inflammatory cell infiltration in the renal interstitium was occasionally seen, and the brownish yellow calcium oxalate crystals did not decrease significantly.

The Evaluation table for Kidney Lesions was as follows:

TABLE 3.3.1

Evaluation table for Kidney Lesions

| Group | Renal tubule dilation lesions | Renal interstitial inflammatory cell infiltration | Calcium oxalate crystal aggregation |
|---|---|---|---|
| Normal group | − | − | − |
| Model group | +++ | ++ | +++ |
| Potassium sodium hydrogen citrate group | ++ | + | ++ |
| Low dose group | ++ | − | ++ |
| Middle dose group | + | − | + |
| High dose group | + | − | + |

Note:
No lesion was represented by −, mild lesion was +, lesion was ++, significant lesion was +++.

Based on the above-mentioned animal pharmacological test results, it is fully proved that the active ingredient extracts of *Polygala japonica* Houtt. in the middle dose group and high dose group in the present invention (the compound after the water extract is eluted with 0-25% ethanol by the polyamide resin column) are all significantly better than those of potassium sodium hydrogen citrate of the same quality from three key indicators for the treatment of nephrolithiasis (calcium oxalate crystal aggregation, renal tubule dilation lesions, and chronic renal interstitial inflammatory cell infiltration). Their drug efficacy level has reached the requirements of Chinese drug registration evaluation, which shows that they have excellent potential and market prospects in the treatment of urolithiasis and urinary tract infections or kidney damage caused by urolithiasis and as an adjuvant drug after surgical treatment of urolithiasis.

Beneficial Effect

The drug of the present invention has significantly better effects than potassium sodium hydrogen citrate in typical test indicators such as calcium oxalate crystal aggregation, renal interstitial inflammatory cell infiltration, and renal tubule dilation lesions, and their drug efficacy level has reached the requirements of Chinese drug registration evaluation, which shows that they have excellent potential and market prospects in the treatment of urolithiasis and urinary tract infections or kidney damage caused by urolithiasis and as an adjuvant drug after surgical treatment of urolithiasis.

Compared with the most widely used clinical drug potassium sodium hydrogen citrate, since the active ingredients (I)~(III) contained in the extract of *Polygala japonica* Houtt. of the present invention do not contain sodium and potassium ions, they will not lead to serious side effects such as severe hyperkalemia, arrhythmia, and hypertension similar with potassium sodium hydrogen citrate, and have better safety.

Compared with other Chinese herbal medicines and drug extracts used for treating diseases related to urolithiasis, the pharmaceutical active ingredient extract of the present invention has simpler components, clearer structure of active ingredients, and more stable and controllable quality.

In addition, the pharmaceutically active ingredient extract of the present invention is preferably extracted from the aboveground part stems and leaves of the *Polygala japonica* Houtt., so as to avoid the problem of excessively long growth cycle of pharmaceutical plants caused by the extraction of the whole herb, with lower cost and better environmental protection.

In summary, the drug of the present invention has clear curative effect on urolithiasis and other related diseases, less side effects (equivalent to or better than the existing mainstream drug for urolithiasis, potassium sodium hydrogen citrate), low cost, simple process, safe and effective, stable and controllable quality, meets modern drug registration requirements, and has excellent medical value and economic value.

The invention claimed is:

1. A method for treating urolithiasis and urinary tract infections or kidney damage caused by urolithiasis in a subject, wherein the method comprises administering to the subject an effective amount of the pharmaceutically active ingredient extract extracted from the plant *Polygala japonica* Houtt, or as an adjuvant drug after surgical treatment of urolithiasis, and wherein the extract comprises:

(a) one or more flavonol compounds selected from the compounds of the following general formula (F-7K), (F-7Q), (F-74Q), (F-K), (F-Q), and (F-74K) as the first active ingredient:

(F-7K)

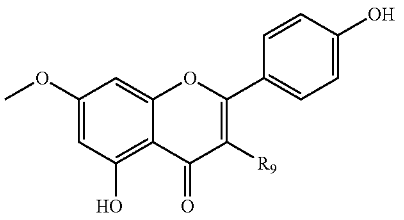

wherein, $R_9$ is selected from the group consisting of —OH, —O-Glc, —O-Gal, —O-Glc-Glc, —O-Glc-Gal, —O-Glc-Rha, —O-Gal-Glc, —O-Gal-Gal, —O-Gal-Rha, —O-Glc-Glc-Api, —O-Gal-Glc-Api, —O-Glc-Gal-Api, and —O-Gal-Gal-Api, (F-7Q)

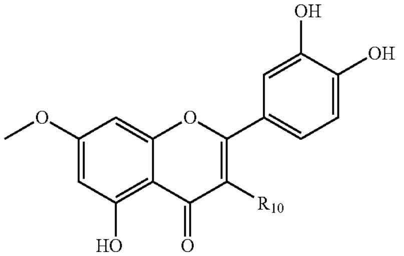

wherein, $R_{10}$ is selected from the group consisting of —OH, —O-Glc, —O-Gal, —O-Glc-Glc, —O-Glc-Gal, —O-Glc-Api, —O-Glc-Rha, —O-Gal-Glc, —O-Gal-Gal, —O-Gal-Api, —O-Gal-Rha, —O-Glc-Glc-Api, —O-Gal-Glc-Api, —O-Glc-Gal-Api, —O-Gal-Gal-Api, —O-Gal-Rha-Gal, —O-Gal-Rha-Glc, —O-Glc-Rha-Glc, and —O-Glc-Rha-Gal, (F-74Q)

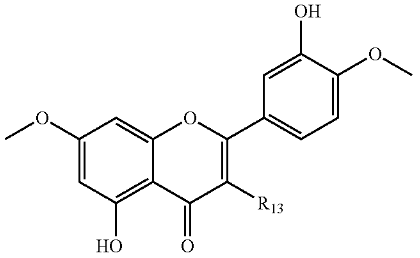

wherein, $R_{12}$ is selected from the group consisting of —OH, —O-Glc, —O-Gal, —O-Glc-Api, —O-Gal-Api, (F-7Q-1)

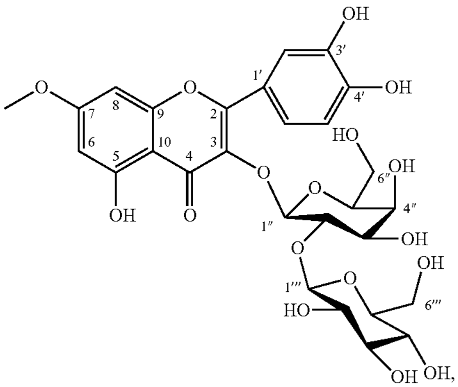

(F-7K-1)

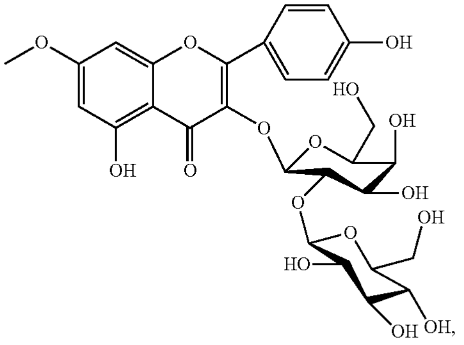

(F-K)

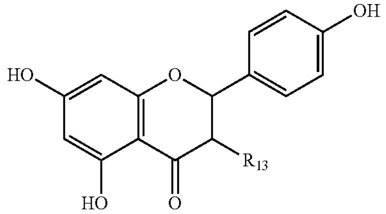

wherein, $R_{13}$ is selected from the group consisting of —OH, —O-Glc, —O-Gal, —O-Glc-Rha, and —O-Gal-Rha, (F-74K)

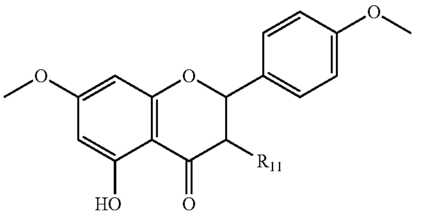

wherein, $R_{11}$ is selected from the group consisting of —OH, —O-Gal, and —O-Gal-Api; and wherein the total content of the flavonol compound of the first active ingredient (a) accounts for 75-100% of the total extract of *Polygala japonica* Houtt, wherein the component content (%) is the HPLC % content calculated by using the HPLC integral area normalization method according to the common method in the art.

2. The method of claim 1, wherein the first active ingredient (a) is at least one selected from the following compounds:

(F-74Q-1)

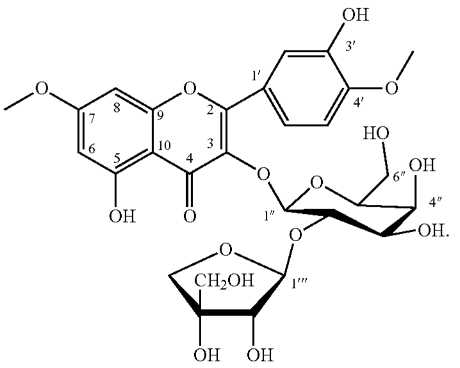

3. A method for treating urolithiasis and urinary tract infections or kidney damage caused by urolithiasis in a subject, wherein the method comprises administering to the subject an effective amount of a pharmaceutical composition or as an adjuvant drug after surgical treatment of urolithiasis; and wherein the pharmaceutical composition comprises at least one compound selected from the following formulas as an active ingredient:

(F-7Q-1)

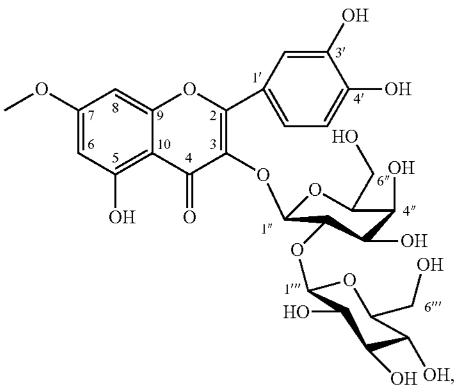

-continued (F-7K-1)

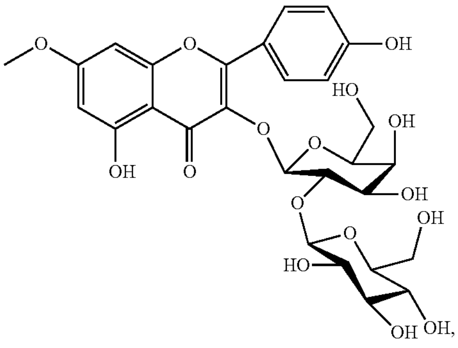

(F-74Q-1)

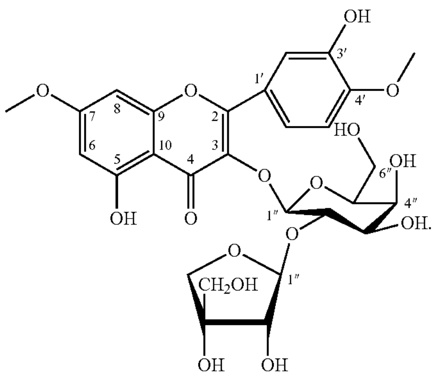

4. A method for treating urolithiasis and urinary tract infections or kidney damage caused by urolithiasis in a subject, wherein the method comprises administering to the subject an effective amount of any one of the following compounds or as an adjuvant drug after surgical treatment of urolithiasis, (F-7Q-1)

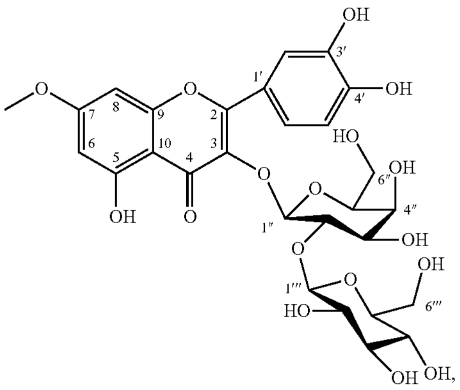

-continued (F-7K-1)

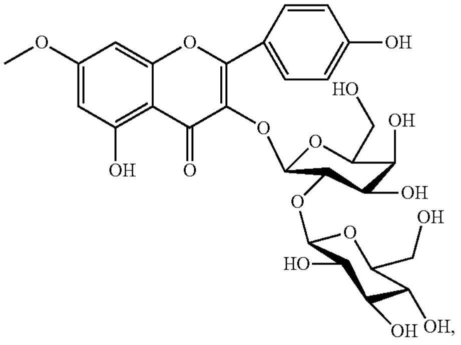

(F-74Q-1)

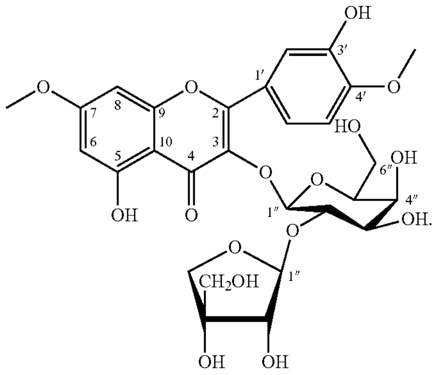

5. The method of claim 1, wherein the extract further comprises:

(b) one or more xanthone compounds selected from the following formulas (II-1), (III-2) and (II-3) as the second active ingredient:

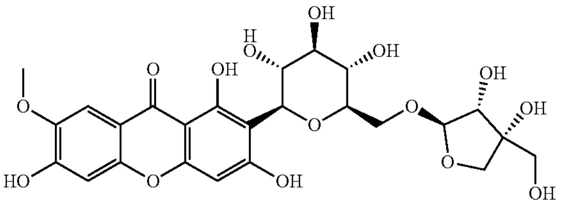 [SMILES: COc1cc2c(=O)c3c(O)c([C@@H]4O[C@H](CO[C@@H]5OC[C@](O)(CO)[C@H]5O)[C@@H](O)[C@H](O)[C@H]4O)c(O)cc3oc2cc1O]

(II-1, polygalaxanthone III)

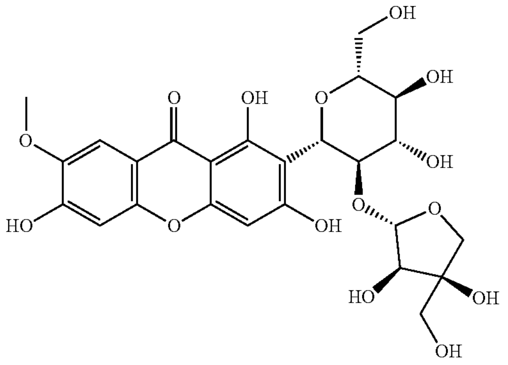 [SMILES: COc1cc2c(=O)c3c(O)c([C@@H]4O[C@H](CO)[C@@H](O)[C@H](O)[C@H]4O[C@@H]4OC[C@](O)(CO)[C@H]4O)c(O)cc3oc2cc1O]

(II-2, polygalaxanthone XI)

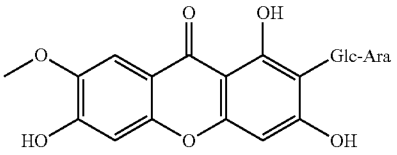

(II-3, polygalaxanthone VIII).

6. The method of claim 1, wherein the extract further comprises:

(c) a glycolipid compound selected from the following formula (III-1) and (III-2) as the third active ingredient:

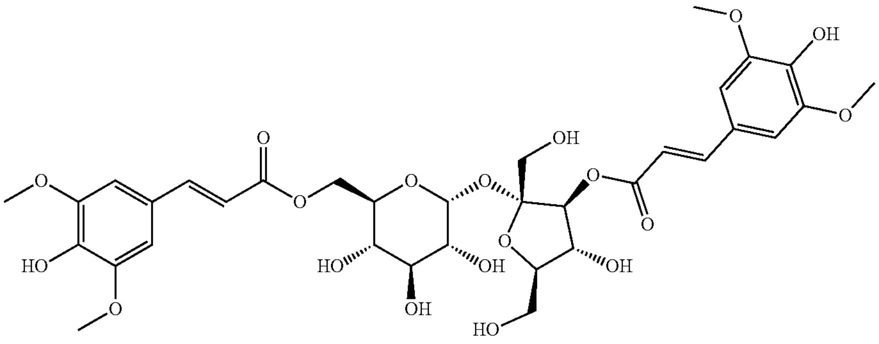

(III-1, 3,6'-disinapoyl sucrose)

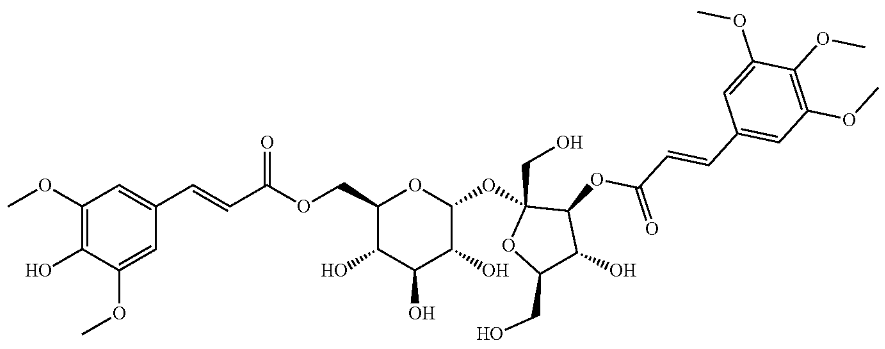
(III-2, Tenuifoliside C).
7. The method of claim 3, wherein the pharmaceutical composition further comprises a pharmaceutically acceptable carrier, excipient or auxiliary material.
* * * * *